(12) United States Patent
Siedenburg et al.

(10) Patent No.: US 11,832,914 B2
(45) Date of Patent: Dec. 5, 2023

(54) METHODS AND SYSTEMS FOR PATIENT PARAMETER FUSION AND FEEDBACK

(71) Applicant: Physio-Control, Inc., Redmond, WA (US)

(72) Inventors: Clinton T. Siedenburg, Everett, WA (US); Tyson G. Taylor, Bothell, WA (US); Robert G. Walker, Seattle, WA (US); Fred W. Chapman, Newcastle, WA (US)

(73) Assignee: Physio-Control, Inc., Redmond, WA (US)

( * ) Notice: Subject to any disclaimer, the term of this patent is extended or adjusted under 35 U.S.C. 154(b) by 419 days.

(21) Appl. No.: 17/075,041

(22) Filed: Oct. 20, 2020

(65) Prior Publication Data

US 2021/0113086 A1 Apr. 22, 2021

Related U.S. Application Data

(60) Provisional application No. 62/924,362, filed on Oct. 22, 2019.

(51) Int. Cl.
*A61B 5/00* (2006.01)
*A61B 5/0205* (2006.01)
(Continued)

(52) U.S. Cl.
CPC ........ *A61B 5/0024* (2013.01); *A61B 5/02055* (2013.01); *A61B 5/082* (2013.01);
(Continued)

(58) Field of Classification Search
CPC .............. A61B 5/0024; A61B 5/02055; A61B 5/082; A61B 5/1116; A61B 5/14542; A61B 5/7221; A61B 5/743
See application file for complete search history.

(56) References Cited

U.S. PATENT DOCUMENTS

2011/0264165 A1* 10/2011 Molnar .............. A61N 1/36185
607/45
2016/0345874 A1* 12/2016 Raisoni ................ A61B 5/0022
(Continued)

FOREIGN PATENT DOCUMENTS

WO WO-2019118027 A1 * 6/2019 ........... A61B 5/0002

*Primary Examiner* — Michael W Kahelin
(74) *Attorney, Agent, or Firm* — McDonnell Boehnen Hulbert & Berghoff LLP

(57) ABSTRACT

An example method is performed by a computing device executing instructions stored in data storage, and includes receiving physiologic monitoring data from a plurality of sensors coupled to a patient, receiving information indicating a measurement of patient motion during the patient care event, determining whether the measurement of patient motion is above a threshold, based on determining whether the measurement of patient motion is above the threshold, generating, for the physiologic monitoring data, a respective quality indicator, analyzing, by the computing device, (i) a combination of the physiologic monitoring data from the plurality of sensors and (ii) the respective quality indicator for the physiologic monitoring data to generate a response dependent upon the combination of the physiologic monitoring data as weighted by the respective quality indicator, and based on analyzing, outputting caregiver feedback by the computing device according to the response.

26 Claims, 14 Drawing Sheets

(51) Int. Cl.
*A61B 5/08* (2006.01)
*A61B 5/11* (2006.01)
*A61B 5/145* (2006.01)

(52) U.S. Cl.
CPC ........ *A61B 5/1116* (2013.01); *A61B 5/14542* (2013.01); *A61B 5/721* (2013.01); *A61B 5/7221* (2013.01); *A61B 5/743* (2013.01)

(56) References Cited

U.S. PATENT DOCUMENTS

2017/0300653 A1* 10/2017 Hresko .................. G16H 40/60
2019/0224434 A1* 7/2019 Silver .................... A61H 31/00

* cited by examiner

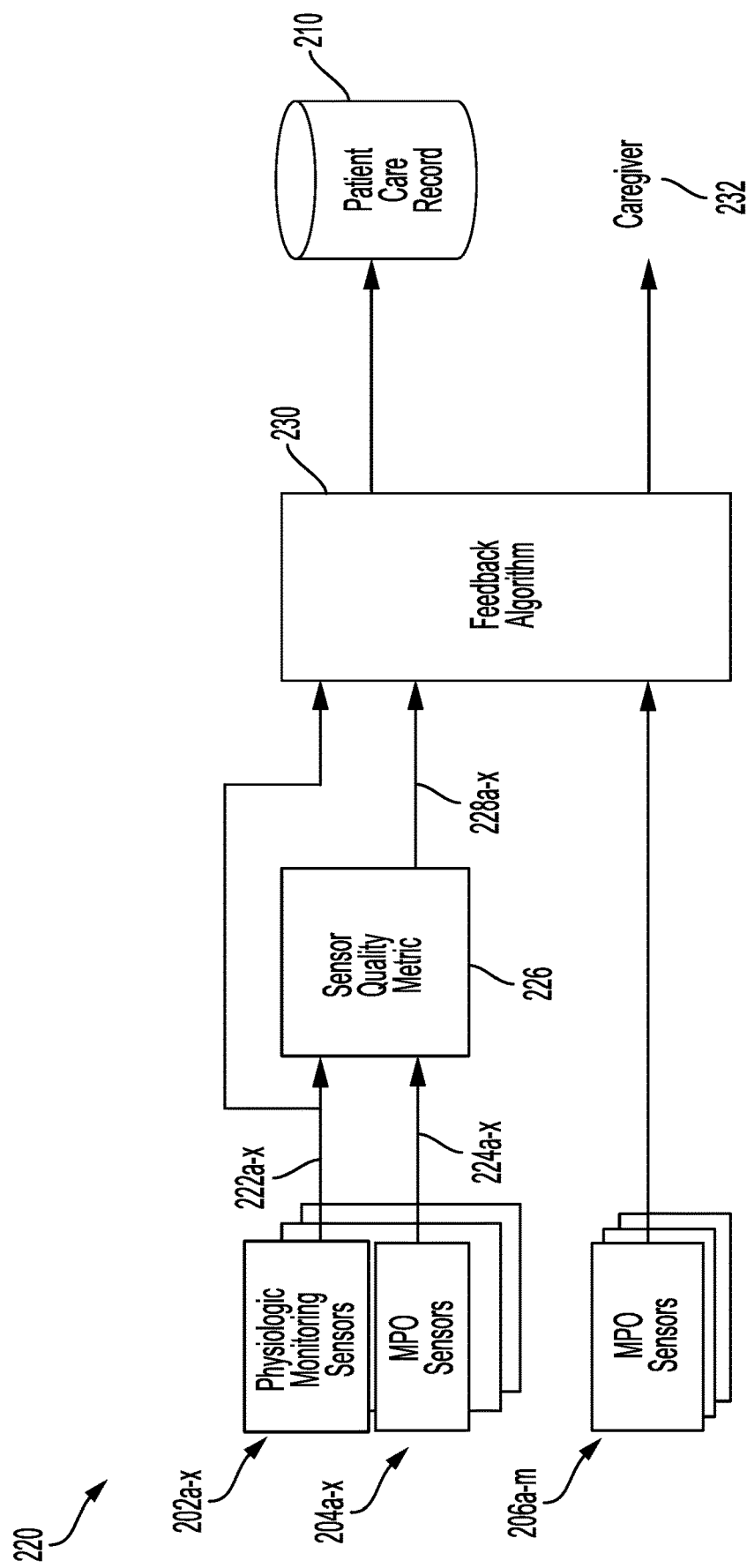

METHODS AND SYSTEMS FOR PATIENT PARAMETER FUSION AND FEEDBACK

CROSS-REFERENCE TO RELATED APPLICATION

The present application claims priority to U.S. provisional application No. 62/924,362, filed on Oct. 22, 2019, the entire contents of which are herein incorporated by reference.

BACKGROUND

Accurate physiologic monitoring, especially of patient vital signs, is a critical part of providing healthcare to patients. In an emergency situation, such as during intubation or providing cardiopulmonary resuscitation (CPR), patients may be connected to a variety of sensors making various physiologic measurements including electrocardiogram (ECG), pulse oximetry (SpO2), capnography (CO2), carbon monoxide (CO), methemoglobin (SpMet), non-invasive blood pressure (NIBP), invasive blood pressure (IP), core body temperature, and so forth. Current art is to receive feedback individually from these sensors to monitor a status of the patient and guide the emergency caregiver in next steps of care.

Emergency care in the field is often performed in varied and chaotic environments and where life and death decisions must be correctly made within moments of arrival of emergency personnel for good patient outcomes. Feedback from the sensors typically used, however, is individually received and interpreted. Few techniques exist for combining patient parameters to give feedback to the healthcare field provider so as to provide context-driven alarms, or other context-enhanced information about a patient care event, generated from the feedback. Due to the awkward, varied, and chaotic environments encountered, physiologic monitoring signals are often corrupted due to motion, unintentional misuse, partial equipment failure, equipment or disposable breakage, among other things. These corrupted signals can then lead to the wrong healthcare decisions or delay the correct ones. Signals can also be misinterpreted even when they are not corrupted, for example, due to insufficient context about the patient or patient care event. This can occur both with uses of the signals, such as algorithms and alarms, that support real time care of the patient by a caregiver, as well as with uses of the signals by algorithms or individuals that are remote in time and/or location from the patient care event. As an example of the latter, an individual who is reviewing physiologic monitoring data that was previously recorded during an earlier patient care event may not accurately interpret the cause, meaning or implications of a portion of physiologic monitoring data because they do not know details such as the position, orientation, motion, or level of physical activity of the patient at the time that the physiologic monitoring data was recorded. Corrupted signals, or signals that are ambiguous due to a lack of context, can thus be a problem for both individuals (e.g. caregivers, data reviewers) and machines (e.g. algorithms, alarms, etc.), for both real time and post-event uses of the signals, both at the location of patient care as well as in places remote from the location of patient care.

Existing solutions found in hospital care generally including receiving multiple patient parameters and implementing algorithms to predict when a patient will "crash" (e.g., experience a rapid declining status such as a drop in blood pressure, a loss of airway patency, inadequate respiration, lack of perfusion of major organs, etc.).

However, it is desirable to utilize all collected data of a patient during treatment of a patient to provide more robust clinical feedback helpful to a healthcare provider for improving treatment of the patient.

SUMMARY

Within examples described herein, systems and methods are described that include analyzing a combination of physiologic monitoring data from a plurality of sensors and outputting caregiver feedback.

Within additional examples described herein, systems and methods are described that include determining a correlation between physiologic monitoring data and outputting caregiver feedback.

The features, functions, and advantages that have been discussed can be achieved independently in various examples or may be combined in yet other examples. Further details of the examples can be seen with reference to the following description and drawings.

BRIEF DESCRIPTION OF THE FIGURES

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying drawings, wherein:

FIG. 4 is a block diagram illustrating an example algorithm for qualifying outputs from the sensors, according to an example implementation.

DETAILED DESCRIPTION

Disclosed examples will now be described more fully hereinafter with reference to the accompanying drawings, in which some, but not all of the disclosed examples are shown. Indeed, several different examples may be described and should not be construed as limited to the examples set forth herein. Rather, these examples are described so that this disclosure will be thorough and complete and will fully convey the scope of the disclosure to those skilled in the art.

Example methods and systems describe various combinations of sensor outputs of an advanced life support (ALS) device that are combined and analyzed to provide feedback for improving patient treatment in situations including intubation, ventilation, and CPR, to name a few. In one example, the various combinations of sensor outputs can be combined to provide detection for return of spontaneous circulation (ROSC) and sepsis. Furthermore, methods describe how to identify which signals are of sufficient quality and which may be corrupted, make use of that information in improving patient treatment feedback, and alert the caregiver of equipment failure or application.

The feedback can be delivered to the healthcare provider or user as either helpful tips or alarms or as control signals to change operation of the device. The types of sensors include a full sensor suite and can be expanded with other autonomous analyzers (e.g., blood gas, blood ion, gene sequencer, audio, video, etc.). Any of the sensors may be wireless or operating independent of a physical connection to a monitor as well eliminating cables and hoses.

Thus, within examples, parameter fusion can provide further insight into patient healthcare, as well as whether treatment is effective (e.g., intubation improper, CPR not working, etc.). Many examples exist for various combinations of outputs of sensors and algorithms for execution resulting in specific types of feedback that can be provided.

Figure 1:
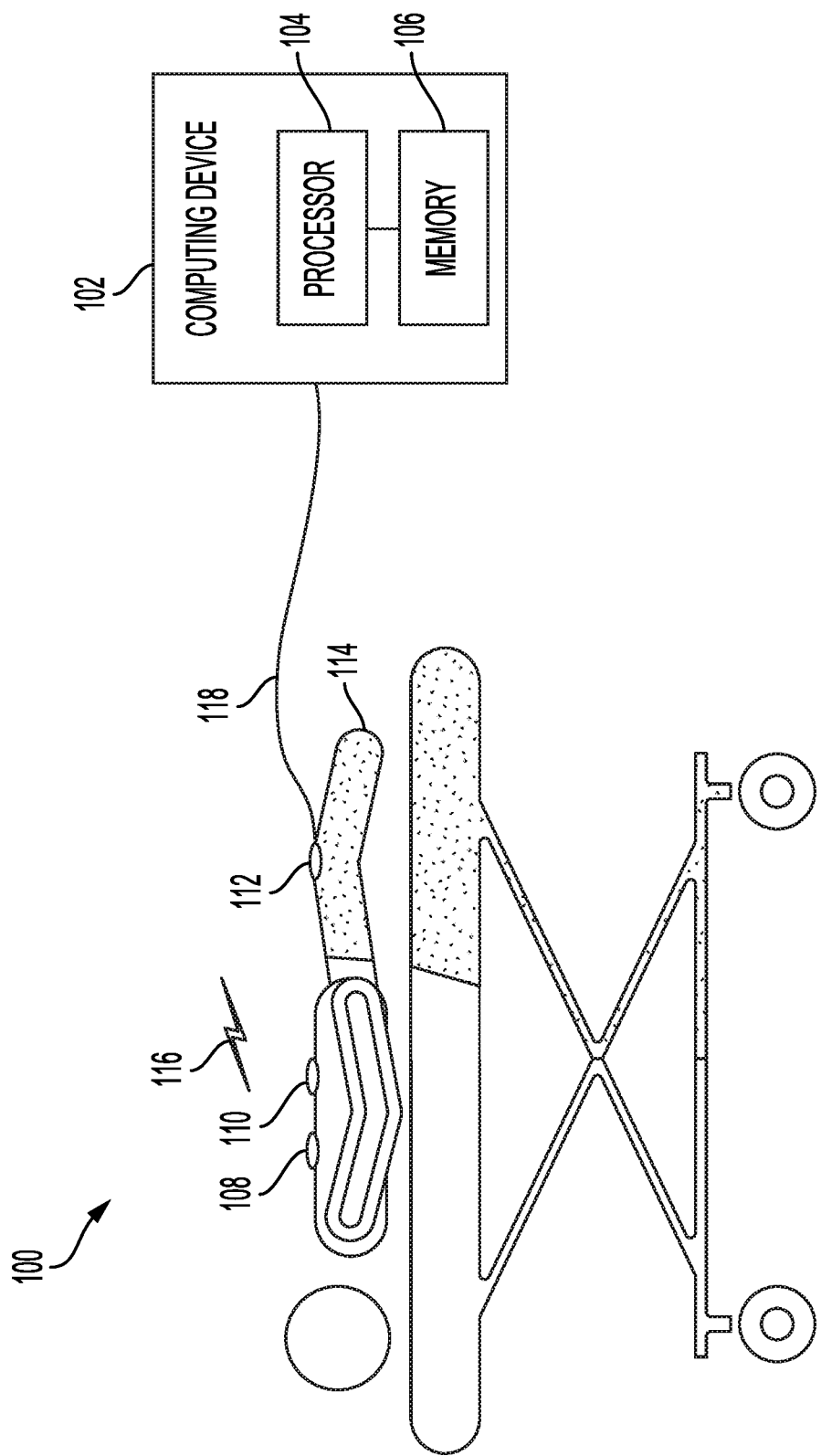
FIG. 1 illustrates an example system for collecting physiologic monitoring data, including vital sign data, from a patient, according to an example implementation.

Referring now to the figures, FIG. 1 illustrates an example system 100 for collecting physiologic monitoring data, including vital sign data, from a patient, according to an example implementation. The system 100 includes a computing device 102 with a processor 104 coupled to memory 106 that is in communication with a plurality of sensors 108, 110, and 112 which are each coupled to or directly connected to a patient 114. The communication may be wireless, such as through a wireless communication link 116 with the sensors 108 and 110, or wired such as through a wired communication link 118 with the sensor 112.

The memory 106 includes a non-transitory computer-readable medium having stored therein a plurality of executable instructions, which when executed by the computing device 102 having the processor 104 causes the computing device 102 to perform functions. For example, the processor 104 is adapted to execute the plurality of executable instructions to receive outputs of the plurality of sensors 108, 110, and 112, and process the outputs to determine feedback to provide to a care provider. The feedback may be audio, visual, or haptic, and thus, the computing device 102 may further include speakers, a display, and a vibrator (not shown).

The plurality of sensors 108, 110, and 112 output physiologic monitoring data measurements to the computing device 102. Any number or type of sensors may be used depending on treatment or monitoring of the patient 114. In many instances, a variety of sensors are used to determine a variety of physiologic monitoring data. Physiologic monitoring data can include vital sign data (e.g., heart rate, respiration rate, blood pressure, and body temperature), as well as signals from other sensors described herein. In addition, physiologic monitoring data can also include treatment monitoring data, such as location at which an endotracheal tube has been placed or other sensor context information. The physiologic monitoring data can include timestamps associated with a time of collection and may be considered a measurement at a specific time. In some instances herein, physiologic monitoring data refers to one measurement and data associated with the one measurement, and in other instances, physiologic monitoring data refers to a collection of measurements as context indicates.

Example sensors include a temperature sensor to provide information indicative of a temperature at the plurality of sensors, a light sensor to provide information indicative of ambient light at the plurality of sensors, a camera to provide images indicative of placement of a tube for intubation in the patient 114, a carbon dioxide detector to provide an indication of carbon dioxide expelled by the patient 114, a microphone to provide an indication of sounds in the tube, a gas detector to provide an indication of presence of gases in the tube, a pressure sensor to provide an indication of airflow pressure in a tube for intubation in the patient 114, an air flow sensor to provide an indication of airflow in the tube, a pulse oximetry sensor to provide a measure of blood oxygenation in the patient 114, an oxygen sensor to provide an indication of oxygen inhaled and exhaled by the patient 114, an effective metabolic sensor (resulting from a combination of outputs from multiple sensors, such as an airway pressure sensor, airflow sensor, and capnography sensor, for example) to provide an indication of a metabolic rate of the patient 114, a blood pressure sensor to provide an indication of a blood pressure of the patient 114, a depth sensor to provide an indication of a depth of compression applied during cardiopulmonary resuscitation (CPR), an ultrasound sensor to provide an indication of vessel area and flow profile over time, external pressure sensors to provide tactile pressure applied to a chest of a patient during cardiopulmonary resuscitation (CPR), external ultrasound sensors to provide an indication of a location of a heart of the patient 114 and/or to assess whether the wall of the heart is moving, an electrocardiogram (ECG) sensor to provide one or more cardiac electrical signals, a lactate sensor to provide an indication of an analysis of blood of the patient 114, and a temperature sensor to provide an indication of patient temperature. Other types of sensors are possible as well to measure other physiologic monitoring data or vital signs of the patient 114.

In addition, the plurality of sensors 108, 110, and 112 include motion, position, and/or orientation (MPO) sensors to provide information indicating a measurement of patient motion during the physiologic monitoring data collection (e.g., during the patient care event). The MPO sensors may be integrated with each or some of the plurality of sensors 108, 110, and 112, or the MPO sensors may be external from the plurality of sensors 108, 110, and 112.

Moreover, the plurality of sensors 108, 110, and 112 can include communication interfaces to enable communication with the computing device 102 either over the wireless communication link 116 or the wired communication link 118. The communication interfaces can thus include transmitters and receivers or output ports, for example.

The computing device 102 may take many forms and may include other components. In one example, the computing device 102 is a monitor module or a therapy module. An example therapy module includes a defibrillator or an automated external defibrillator (AED).

Figure 2:
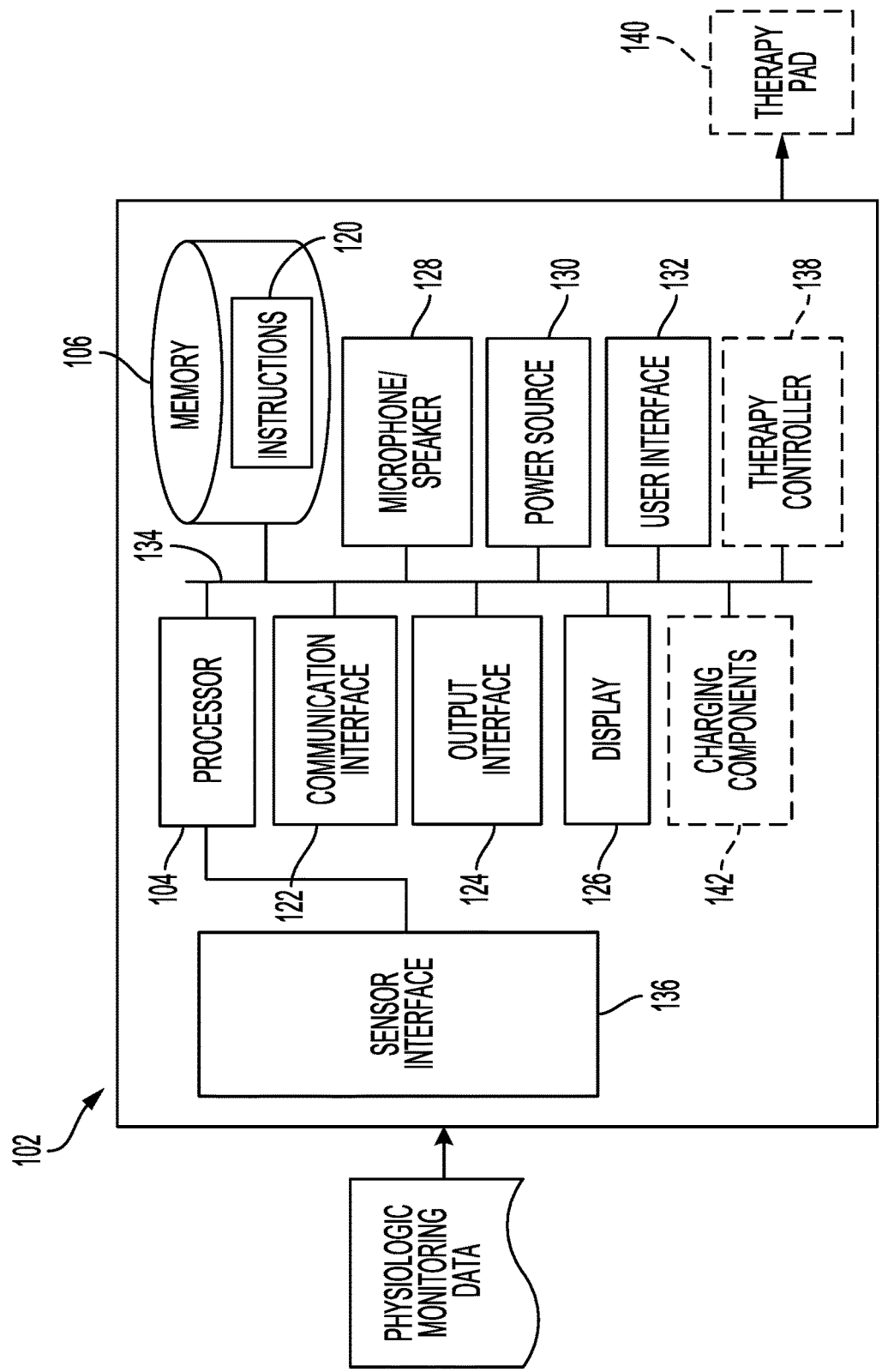
FIG. 2 illustrates a block diagram of an example of the computing device, according to an example implementation.

FIG. 2 illustrates a block diagram of an example of the computing device 102, according to an example implementation. In FIG. 2, the computing device 102 includes the processor 104, and the memory 106 storing instructions 120, that when executed by the processor 104, causes the processor 104 to perform functions of the monitor or therapy module.

To perform the functions, the computing device 102 includes a communication interface 122, an output interface 124, a display 126, a microphone/speaker 128, a power source 130, and a user interface 132, and each component of the computing device 102 is connected to a communication bus 134. The computing device 102 also includes a sensor interface 136.

The communication interface 122 may be one or more wireless interfaces and/or one or more wireline interfaces that allow for both short-range communication and long-range communication to one or more networks or to one or more remote devices. Such wireless interfaces may provide for communication under one or more wireless communication protocols, Bluetooth, Bluetooth low-energy (BLE), Wi-Fi (e.g., an institute of electrical and electronic engineers (IEEE) 802.11 protocol), Long-Term Evolution (LTE), cellular communications, near-field communication (NFC), and/or other wireless communication protocols. Such wireline interfaces may include an Ethernet interface, a Universal Serial Bus (USB) interface, or similar interface to communicate via a wire, a twisted pair of wires, a coaxial cable, an optical link, a fiber-optic link, or other physical connection to a wireline network. Thus, the communication interface 122 may be configured to receive input data from the plurality of sensors 108, 110, and 112 and may also be configured to send output data to other devices. The communication interface 122 thus may include hardware to enable communication between the computing device 102 and other devices (not shown). The hardware may include transmitters, receivers, and antennas, for example. The communication interface 122 may also be capable of operating as a wireless access point as well.

The memory 106 may include one or more computer-readable storage media that can be read or accessed by the processor 104. The computer-readable storage media can include volatile and/or non-volatile storage components, such as optical, magnetic, organic or other memory or disc storage, which can be integrated in whole or in part with the processor 104. The non-transitory data storage is considered non-transitory computer readable media. In some examples, the non-transitory data storage can be implemented using a single physical device (e.g., one optical, magnetic, organic or other memory or disc storage unit), while in other examples, the non-transitory data storage can be implemented using two or more physical devices.

The non-transitory data storage thus is a computer readable medium, and instructions 120 are stored thereon. The instructions 120 include computer executable code.

The processor 104 may be general-purpose processors or special purpose processors (e.g., digital signal processors, application specific integrated circuits, etc.). The processor 104 may receive inputs from the communication interface 122 as well as from other sensors and process the inputs to generate outputs that are stored in the non-transitory data storage. The processor 104 can be configured to execute the instructions 120 (e.g., computer-readable program instructions) that are stored in the non-transitory data storage and are executable to provide the functionality of the monitor or therapy module described herein.

The output interface 124 outputs information for reporting or storage, and thus, the output interface 124 may be similar to the communication interface 122 and can be a wireless interface (e.g., transmitter) or a wired interface as well.

The display 126 includes a touchscreen or other type of display. The microphone/speaker 128 include capabilities to receive audio/voice instructions, and to output audio including audible prompts.

The power source 130 may include battery power, or a wired power means such as an AC power connection.

The user interface 132 provides indicator LEDs for readiness status and power, to support failure analysis, operations, service, as well as software debugging. The user interface 186 may include Ethernet and USB ports as well.

The sensor interface 136 enables the plurality of sensors 108, 110, and 112 to be magnetically attached, for example, to a housing of the computing device 102 for storage. Each sensor module has a small magnet that will activate a Hall Effect sensor in the sensor interface 136 indicating the presence of a sensor module. When the arrival of a sensor module is detected, the computing device 102 emits the field that activates the passive near-field communication (NFC) mechanism of the sensor and determines what type of sensor it is, queries its status such as power remaining, and preemptively pairs with the computing device 102. When the Hall Effect sensor indicates that the sensor is being removed, the computing device 102 activates the sensor module power through NFC. In this way, pairing of sensor to monitor will be unnoticed and sensor battery power will be conserved.

The computing device 102 can also include other components to operate as a therapy module, such as a therapy controller 138 that connects to therapy pads 140 and charging components 142. The therapy pads 140 are disposable and quickly connect/disconnect with a magnetic connection scheme, for example, to couple to the therapy controller 138. Electrical connection is made to carry the high currents required for defibrillation. The ability to read identification over a serial bus is designed into the connection.

The therapy controller 138 may include a field programmable gate array (FPGA) state machine that receives high level commands from the processor 104. Such commands include charge to a certain energy level, shock, and discharge as well as setting a current level for pacing mode. The therapy controller 138 controls charging and discharging of an energy storage capacitor, detailed operation of the H-bridge, as well as the pacing circuitry that controls the current level within the charging components 142. A second FPGA state machine in the therapy controller 138 may be used to control analog-to-digital conversion of ECG and impedance waveforms so as to not burden the processor 104 with tight timing requirements. A circular buffer in the therapy controller 138 temporarily holds the data and alerts the processor 170 when another packet of predetermined size is available for transfer and processing.

Within one example, in operation, when the instructions 120 are executed by the processor 104, the processor 104 is caused to perform functions including receiving physiologic monitoring data from the plurality of sensors 108, 110, and 112 coupled to the patient 114 during a patient care event, and receiving information indicating a measurement of patient motion during the patient care event. The functions then include determining whether the measurement of patient motion is above a threshold for each sensor of the plurality of sensors 108, 110, and 112 during the physiologic monitoring data measurements, and based on determining whether the measurement of patient motion is above the threshold for each sensor of the plurality of sensors 108, 110, and 112, generating, for the physiologic monitoring data received from each sensor of the plurality of sensors, a respective quality indicator. The functions also include analyzing, by the computing device 102, (i) a combination of the physiologic monitoring data from the plurality of sensors 108, 110, and 112 and (ii) the respective quality indicator for the physiologic monitoring data to generate a response dependent upon the combination of the physiologic monitoring data as weighted by the respective quality indicator, and based on analyzing (i) the combination of the physiologic monitoring data from the plurality of sensors 108, 110, and 112 and (ii) the respective quality indicator for the physiologic monitoring data, outputting caregiver feedback by the computing device according to the response. Thus, each physiologic measurement has its own respective quality indicator, which influences a contribution of that individual physiologic measurement into the caregiver feedback, as well as potentially influences a presence or nature of the overall feedback to caregivers.

A type of feedback is dependent upon a type of the physiologic monitoring data received, which is generally based on the therapy being provided to the patient 114. A number of examples are described below with reference to FIGS. 5A-5G.

Figure 3:
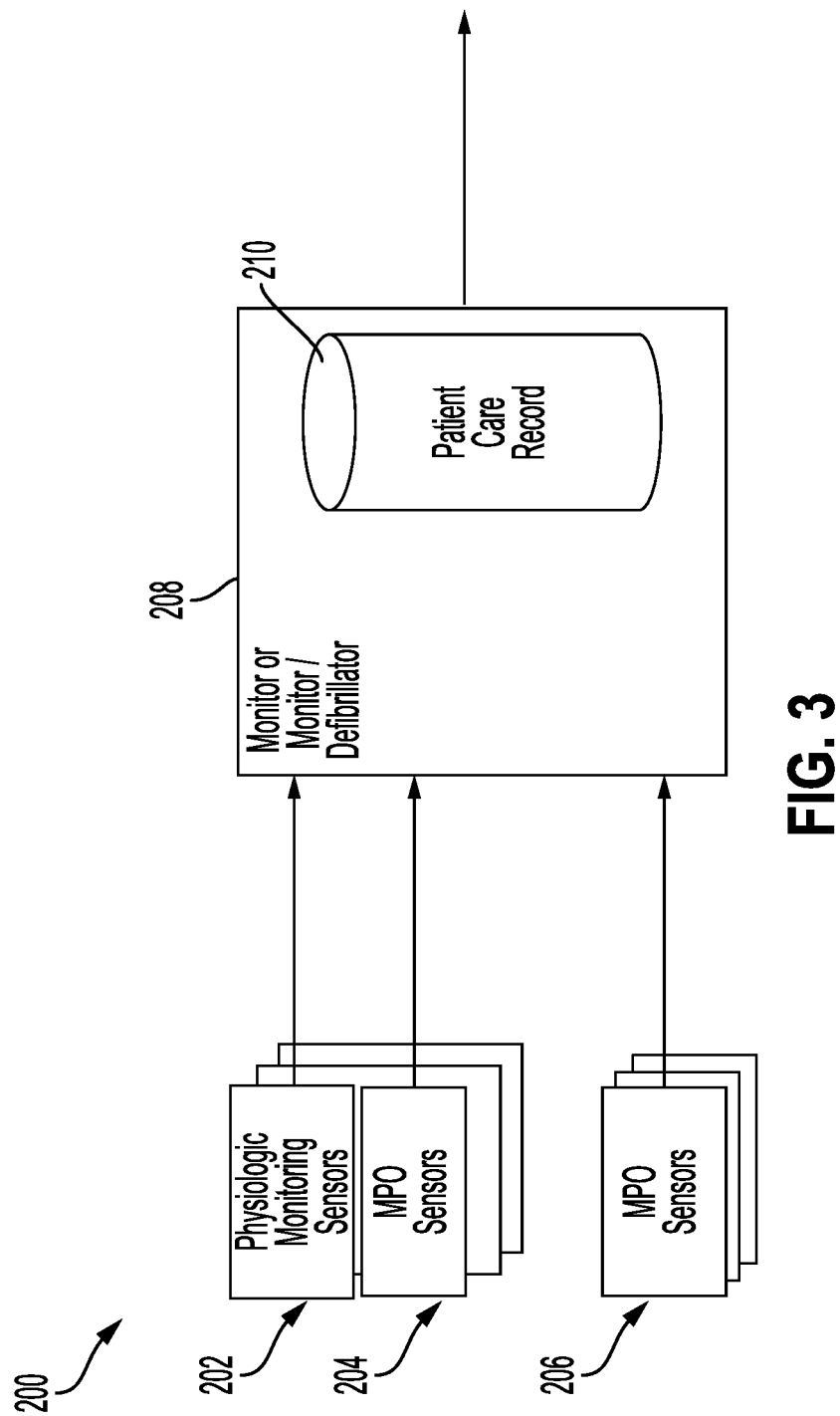
FIG. 3 is a block diagram illustrating an example system for receiving physiologic monitoring data, including vital sign measurements, from a patient and analyzing the measurements to provide caregiver feedback, according to an example implementation.

FIG. 3 is a block diagram illustrating an example system 200 for receiving physiologic monitoring data from a patient 114 and analyzing the measurements to provide caregiver feedback, according to an example implementation. Measurement of sensor and patient motion or position is often lacking during patient treatment, and yet provides an important means of qualification of signal integrity or validity for any sensor as well as information for healthcare professionals further along the chain of care. It is also useful for quality improvement activities and review.

In FIG. 3, an emergency healthcare professional is attending to a patient in distress, and the healthcare professional (e.g., emergency team member) applies physiologic monitoring sensors 202 to a patient. The physiologic monitoring sensors 202 include sensors that measure heart electrical activity such as electrocardiogram (ECG), saturation of the hemoglobin in arterial blood with oxygen (SpO2), carbon monoxide (carboxyhemoglobin, COHb) and/or methemoglobin (SpMet), partial pressure of carbon dioxide (CO2) in gases in the airway by means of capnography, total air pressure in the airway, flow rate or volume of air moving in and out of the airway, blood flow, blood pressure such as non-invasive blood pressure (NIBP) or invasive blood pressure (IP) by means of a catheter, core body temperature with a temperature probe in the esophagus, oxygenation of hemoglobin within a volume of tissue (rSO2), indicating level of tissue perfusion with blood and supply of oxygen provided by that perfusion, and so forth. The physiologic monitoring sensors 202 may include any number or type of sensors described above with respect to FIG. 1. In this example, one or more of the physiologic monitoring sensors 202 are augmented with motion, position, and/or orientation (MPO) sensors 204. The MPO sensors 204 may be built into the physiologic monitoring sensors 202 or may be externally attached to the physiologic monitoring sensors 202. The MPO sensors 204 can include accelerometers, velocimeters, magnetometers, gyros, proximity or distance measuring sensors, triaxial field induction technology, optical technology such as cameras and body cameras which may be used individually or in combination to determine patient or sensor motion, orientation and/or position, particularly the kind of motion that would affect the quality of the physiologic monitoring data.

Other or additional motion, position, and/or orientation (MPO) sensors 206 may be positioned on the patient head, arms, legs, or other places on the body. Furthermore, the MPO sensors 206 could be placed on equipment such as cots, carts, and vehicles. Not only can these sensors contribute to qualification of vital sign signals, but the additional MPO sensors 206 can record patient activity (e.g. shivering, thrashing or immobile) and orientation (e.g. laying down, sitting up, walking, reclined, etc.).

Outputs from the physiologic monitoring sensors 202 and the MPO signals 204 and 206 are conveyed to a monitor 208. The monitor 208 may take the form of the computing device 102 shown in FIG. 2, and can also be a monitor-defibrillator, for example. The monitor 208 records the signals and uses the signals for vital sign qualification and caregiver feedback. The signals can be conveyed to the monitor 208 by wireless means or by wired means. The use of these signals for vital sign qualification and caregiver feedback will be discussed further below. One common concern for sensors that communicate to a monitor by wireless means is loss of wireless connection. An alert can emanate either visually and/or audibly based upon a loss of wireless connection or lack of activity. In some examples, the monitor 208 may send a wireless signal to each of the sensors interrogating the sensors for data, and in response, the monitor 208 receives the physiologic monitoring data from the sensors.

Ultimately, physiologic monitoring data and/or MPO information is recorded in a patient care record 210 of the monitor 208 and delivered to subsequent entities (e.g., hospital emergency department, etc.) via wired or wireless means.

FIG. 4 is a block diagram illustrating an example algorithm 220 for qualifying outputs from the sensors, according to an example implementation. Outputs 222*a-x* from the physiologic monitoring sensors 202 (e.g., multiple sensors referenced as 202*a-x*) and outputs 224*a-x* from the MPO sensors 204*a-x* are first qualified by a sensor quality metric function 226. When corresponding MPO sensors 204*a-x* are present, the sensor quality metric function 226 determines if physiologic monitoring sensor motion is above a particular threshold or sets of thresholds indicating a level of motion causing a quality indicator 228*a-x* generated for that sensor to be flagged as good, degraded, or not useable. The thresholds are unique to each method of motion detection. Within examples, physiologic monitoring data can be previously made under different levels and kinds of motion and detected by the MPO sensors so that thresholds can be identified for that physiologic monitoring sensor and MPO sensor pair. An example implementation is to use an accelerometer measurement as the MPO sensor that is integrated with the physiologic monitoring sensor with their signals interleaved or otherwise time stamped so that the time of motion detected on the accelerometer is readily coordinated with signals on the physiologic monitoring sensor.

The quality indicator 228*a-x* can be generated for and associated with each of the physiologic monitoring data that are received from the physiologic monitoring sensors 202. The quality indicator 228a-x may be a qualitative indicator, such as good, bad, etc., or can be a quantitative indicator, such as a percentage of how much movement was detected. The percentage could then be applied as a weight or modifier to the measurement to discount the measurement accordingly. The quantitative indicator could also be used to generate a numeric confidence interval or "error bars" displayed alongside a given physiologic measurement.

Within examples, the quality indicator can additionally or alternatively be represented via a continuous scale or index, and not based on a simple threshold. Still further, the measurement of patient motion may additionally or alternately include periodic or continuous measurement of the position or orientation of part or all of the patient's body, and generation of a "context" indicator as well indicating what part of the patient's body experienced the specific motion.

Other information may be used during generation of the quality indicator 228a-x, such as a temperature at the physiologic monitoring sensors 202 or an amount and characteristics of ambient light at the physiologic monitoring sensors 202, for example. Some physiologic monitoring sensors 202 may be sensitive to temperature or ambient light, and outputs of those physiologic monitoring sensors can be discounted accordingly using the quality indicator 228a-x.

In addition or alternatively, the patient may be augmented with the MPO sensors 206a-m in lieu of or in addition to the MPO sensors 204a-x. For example, the MPO sensor 206a could be placed sufficiently close to where SpO2 is being measured to qualify the SpO2 signal. In addition to vital sign sensor qualification, the MPO sensors 206a-m can provide information about the activity and orientation of the patient. The use of these signals will be discussed further below.

A feedback algorithm 230 takes on a number of forms depending upon the sensors available. An output of the feedback algorithm 230 is stored in the patient care record 210 of the device which may be delivered with the patient to provider in the next step of the chain of care for the patient. The output may also contain the underlying sensor data upon which the algorithm made its decisions. The feedback algorithm 230 provides status, alerts, alarms, or suggestions to the patient care provider that may be qualified by a qualitative or quantitative confidence indication that may be expressed visually (e.g. alphanumeric symbols, font changes, font colors, symbols, etc.) or audibly (e.g. tones, beeps, etc.) or tactilely (e.g. vibrations, shocks, etc.) on a personal wearable device.

An example type of feedback that may be delivered to a caregiver 232 from the feedback algorithm 230 is a correlation between physiologic monitoring data responses coming from physiologic monitoring sensors 202a-x to positions or movement detected by the MPO sensors 204a-x or 206a-m. The feedback algorithm 230, depending upon the types and locations of MPO sensors, is able to understand if patient positions or movement causes physiologic monitoring data to improve or degrade. For example, the MPO sensor 206b can be a position detector positioned on the patient's forehead, or alternatively, the physiologic monitoring sensor 202a can be an RSO2 with an integrated triaxial field induction (x-y-z position) sensor. Correlation between perfusion and oxygenation measured by the RSO2 sensor and triaxial field induction sensor is analyzed. If there is a substantive change in perfusion level measured by the RSO2 sensor that exceeds a threshold low, the MPO sensor 206b is interrogated around that time to determine if there was a position change of the patient, perhaps sitting up. The feedback algorithm 230 then can alert the caregiver that RSO2 degraded when the patient sat up and suggest that the patient return to the prior condition.

Alternatively, if the MPO sensor 202a or 206a indicates that the motion was of a nature that would corrupt the RSO2 measurement, then the feedback algorithm 230 could wait for a predetermined time before updating RSO2 to the caregiver or indicating low confidence of the displayed measurement. Thus, based on determining that there was the position change of the patient resulting in a corrupted physiologic monitoring data, the caregiver feedback can be paused until the patient motion abates, or the physiologic monitoring data that occurred at the timestamp can be discarded, ignored, flagged, or removed from further processing since the physiologic monitoring data is corrupted.

Another example algorithm includes use of an accelerometer within an NIBP sensor since it is well known that the state of the art NIBP algorithms are notoriously sensitive to motion. Thus, the MPO sensor 204b may be incorporated within the physiologic monitoring sensor 202b that may be an NIBP sensor. When the accelerometer levels exceed a threshold, one of several responses can be invoked. One response is that the NIBP value is discarded. Alternatively, the response may be to ignore that portion of the NIBP waveform that occurred at the same time as the accelerometer measured excessive motion with the algorithm otherwise proceeding in its usual way. A third response is to interrupt the algorithm or restart the algorithm or pause the algorithm until the motion abates. A fourth is to mark it as poor quality due to motion. A fifth is to correct the NIBP waveform where it is corrupted by motion by removing a scaled version of a function derived from a motion sensor waveform in order to remove the motion artifact from the physiologic monitoring data. For example, an accelerometer waveform could be integrated to obtain velocity. A scaling factor for this velocity waveform would be computed such that the disturbance in the NIBP is minimized. All of these responses may occur in real time or near-real time during the patient care event, or at a later time after the patient care event is completed. Additionally, all of these responses may occur at the location(s) of the patient care event, or at locations remote from where patient care occurred.

Similarly, SPO2 measurements suffer as well from motion such as shivering, finger tapping or movement. Just as the NIBP measurement can be modified or qualified as described above, so can a SPO2 measurement.

Figure 5A:
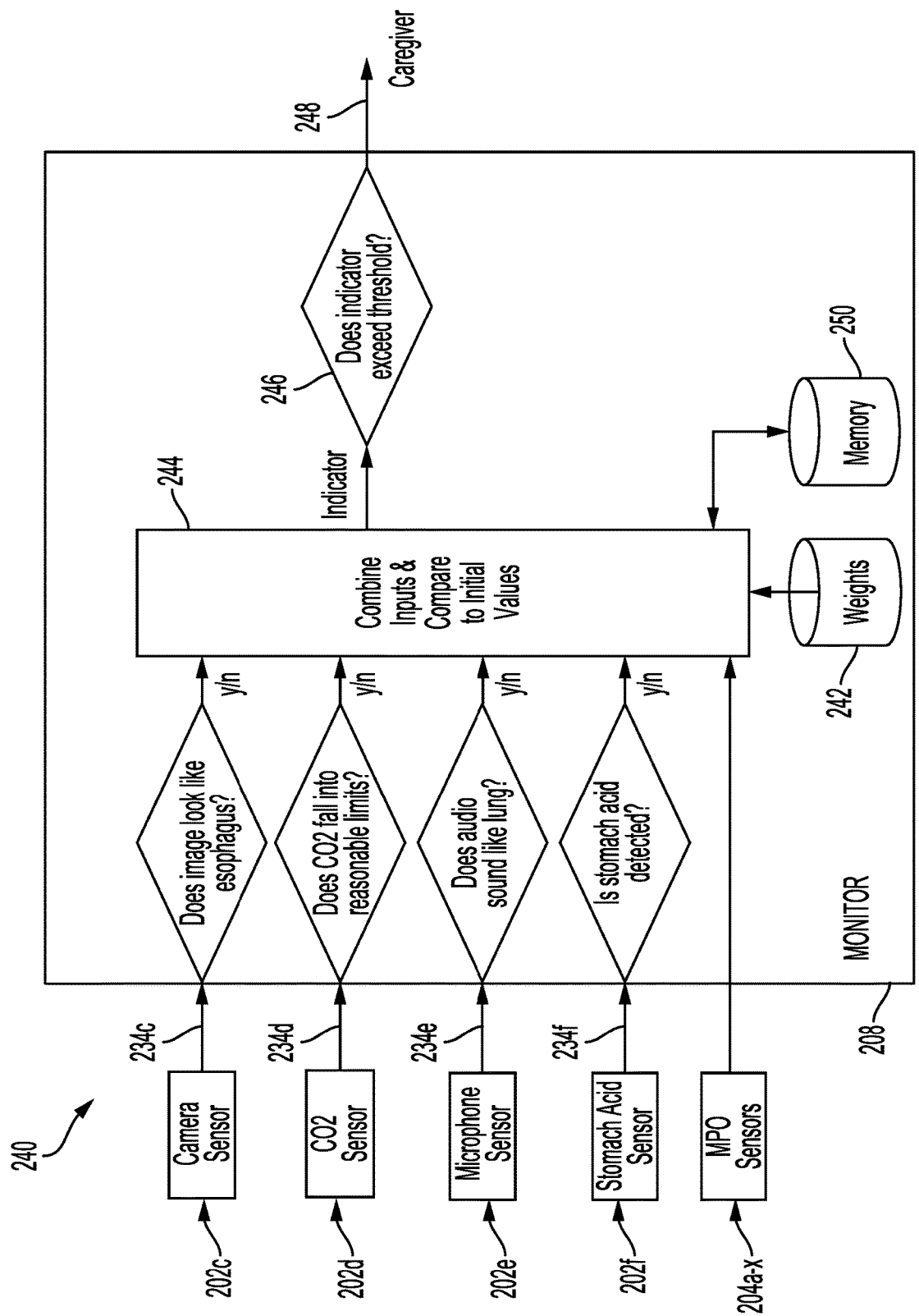
FIG. 5A is a block diagram illustrating an example algorithm for intubation feedback, according to an example implementation.

FIG. 5A is a block diagram illustrating an example algorithm 240 for intubation feedback, according to an example implementation. A useful improvement in emergency patient care in the field is feedback as to (a) whether an intubation tube is properly placed in the trachea (and not the esophagus), and (b) whether the intubation tube has moved out of place since installation. One or more sensors may be used in combination with each other in determining the feedback.

One sensor useful for such feedback is a camera 202c (e.g., such as from a laryngoscope that is equipped to provide video which is typically used for tube placement). The camera 202c, however, is normally not left in the patient. Thus, following placement of the tube, outputs of other sensors can be useful, such as a capnography sensor 202d (e.g., CO2 sensor). Detection of CO2, such as using the capnography sensor 202d using light absorption technology, can be used as an indicator of a properly placed respiration tube on a living person. For measurements out of a normal range, the interpretation may be ambiguous, but such readings can indicate either (a) an improperly placed tube or (b) a seriously ill or dying patient if the patient is properly intubated, which would lead to quite different treatments. This ambiguity can be further resolved through use of outputs of other sensors including a microphone sensor 202e to listen to sounds in the tube. The stomach will sound different than the lung as air is automatically or manually forced into the cavity. Using temporal and spectral characteristic differences between stomach and lung sounds picked up by the microphone sensor 202e, a determination could be made as air is pushed in by manual or automatic ventilation techniques. Finally, presence or lack of gases in a proper concentration or proper waveform can be determined using outputs of a capnography sensor or an pH sensor 202f could be used to detect the presence of stomach acid.

In each case, the sensors 202c-f provide corresponding sensor waveforms 234c-f and output a metric indicative of what that sensor is measuring. The outputs of the sensors 202c-f are provided to the monitor 208, which then determines if the measurement values fall within certain ranges, and yields a logical answer of yes or no, or perhaps a maybe, which can be characterized by a 0 for "no," 1 for "yes," and a value in between for a "maybe." These logical answers may be modified based upon the outputs of the MPO sensors 204a-x, for example, indicating an inordinate motion. The modification is processed via the quality indicator. For example, if there is motion relative to the microphone sensor 202e, that audio data may be discarded by setting a weight for the output of the microphone sensor 202e to zero or "not applicable". Conversely, if there is motion detected on the camera sensor 202c relative to the original placement, then a weight of the output of the camera sensor 202c may be enhanced. The initial weights may be set according to practice if one sensor is a more reliable indicator than another for a particular feedback. In fact, there may be a different set of weights for the same sensors for each feedback response. The monitor 208 may include within data storage a weights database 242 storing all the different weights. A weighted sum of the logical answers can be combined in an algorithm 244, which outputs an indicator for comparison to a threshold 246 to produce a feedback response 248 for a caregiver. There may be a separate set of weights creating separate indicators for comparison to different thresholds for each feedback response 248.

Data over time may be stored in a memory 250 of the monitor 208. This allows the monitor 208 to perform a comparison on original camera sensor data when the intubation was determined visually by the caregiver as correct to a current view as another metric indicating whether there was a change from original placement in addition to whether the image looks like an esophagus. As a result, the feedback 248 can include a notification indicative of whether the tube has moved out of place since installation based on a change in the first set of the physiologic monitoring data to the second set of the physiologic monitoring data.

Figure 5B:
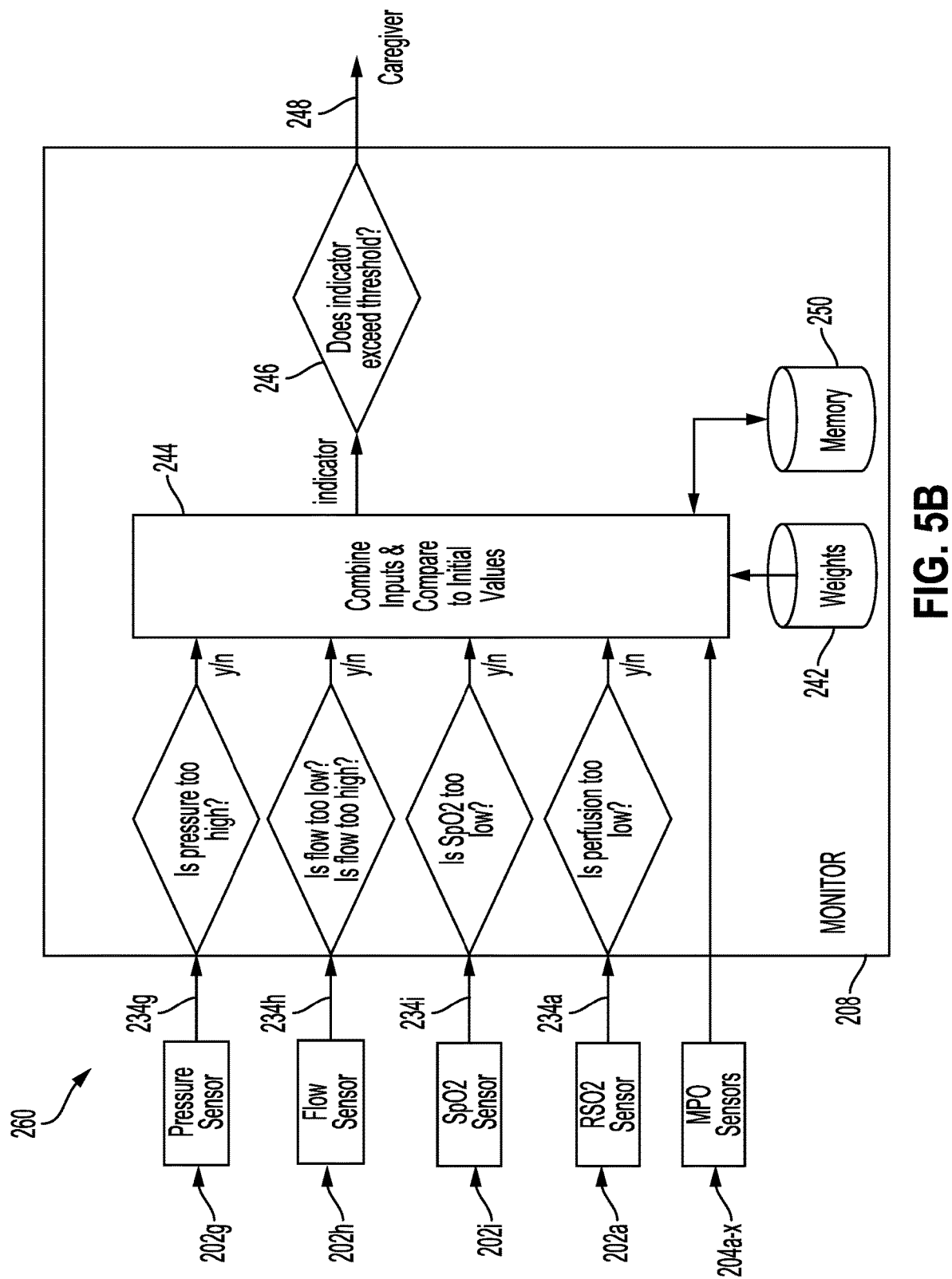
FIG. 5B is a block diagram illustrating an example algorithm for ventilation feedback, according to an example implementation.

FIG. 5B is a block diagram illustrating an example algorithm 260 for ventilation feedback, according to an example implementation. A useful improvement in emergency patient care in the field is feedback as to (a) whether the patient's airway is over pressurized which can cause damage, (b) whether the volume of air is too high which can cause harm, (c) the patient oxygenation is too high which can be harmful, (d) whether the volume of air is too low and the patient oxygenation and ventilation are inadequate, and (e) spontaneous breathing.

One useful sensor for such feedback is that of a pressure sensor 202g used to measure airway pressure. This is important as when manual ventilation is being performed on an intubated patient, too much air pressure can be developed by the caregiver. Another useful sensor is an air flow sensor 202h which can be accomplished by means of an optical, acoustic, or mechanical means as is done by current practices for gases. This is important as user errors often include over ventilating a patient, or by neglecting ventilation activities for too long. An SpO2 sensor 202i can also be used for making a pulse oximetry measurement of blood oxygenation that typically uses light absorption methods at particular frequencies to make its determination, particularly for under oxygenated conditions. A further sensor for this feedback includes the RSO2 sensor, for measuring perfusion and oxygenation of tissue. Still further sensors include sensors for measuring partial pressures of different gasses in the airway such as CO2 (capnography) and O2 these sensors will facilitate determination of appropriate ventilation and oxygenation.

Within this example, the sensors 202a and 202g-i provide corresponding sensor waveforms 234a and 234g-i and output a metric indicative of what that sensor is measuring. The outputs of the sensors 202a and 202g-i are provided to the monitor 208, which then determines if the measurement values fall within certain ranges and yields a logical answer of yes or no, or perhaps a maybe, which can be characterized by a 0 for "no," 1 for "yes," and a value in between for a "maybe." Additionally or alternatively, the monitor 208 utilizes outputs of the sensors 202a and 202g-i and yields continuous or categorical values; for example, a scale of values or categories indicating ventilation is woefully insufficient to extremely over-ventilated. These logical, scalar, or categorical answers may be modified based upon the MPO sensors 204a-x, for example, indicating an inordinate motion. For example, if there is motion relative to the pressure sensor 202g, that pressure data may be discarded by setting a weight for the output of the pressure sensor 202g to zero or "not applicable". This technique may also be used for the other sensors noted. Initial weights may be set according to practice if one sensor is a more reliable indicator than another for a particular feedback. In fact, there may be a different set of weights for the same sensors for each feedback response. A weighted sum of the logical answers can be combined in the algorithm 244, which outputs an indicator from comparison to the threshold 246 to produce the feedback response 248 for the caregiver. There may be a separate set of weights creating separate indicators for comparison to different thresholds for each of the feedback response 248.

It should be noted that spontaneous breathing can be distinguished from artificial positive pressure ventilation by use of a pressure senor to measure airway pressure. This is because spontaneous breathing is driven by generating negative intrathoracic pressure via expansion of the chest cavity where positive pressure ventilation is performed by applying positive pressure to the airway thereby causing lung inflation and hence chest cavity expansion. Such an event can be qualified by outputs of the MPO sensors 204a-x.

Data over time may be stored in the memory 250 of the monitor 208. This allows the monitor 208 to perform a trending analysis of each of the parameters over time. Given slopes of the waveforms 234a and 234g-i, a parallel set of decisions can be made by the monitor 208 executing the algorithm 244 based upon the rates. The decisions for rates can determine if the rate shows the patient falling out of safe limits in a certain amount of time (e.g., 10 minutes). These logical answers concerning trends or rates can be combined as a weighted averaged distinctly for each response desired to produce and indicator, and then compared to a threshold to determine if that particular feedback is to be issued to the caregiver.

It should be further noted that in some examples, the weighted summations are not merely a Bayesian technique, but can be modified to be a Boolean equation depending upon the weights and thresholds used. That is, the weights database 242 storing weights of an individual parameter could be so high (unless negated, for example, by an MPO indicator) that it automatically exceeds the indicator threshold 246. Furthermore, the weights on another pair of parameters might require that they are both true in order to exceed the threshold. In this way, one can create a logical OR function between one parameter and the logical AND of two others. Many other logical equations may be created including the use of the same parameter in different ways with differing weights.

Not only can the indicator which is input to threshold 246 be formed by a linear combination of physiologic monitoring indicators in blocks 244, 272, and 292, but the indicator input to threshold 246 may additionally or alternatively be formed by non-linear means such as min, max, absolute value, power, root, log, and inequalities.

Furthermore, the weights may be determined from first principles or may be determined from machine learning techniques that can, in effect, identify both the equations and the weights required to issue the correct prompts and indicators to the caregiver.

Figure 5C:
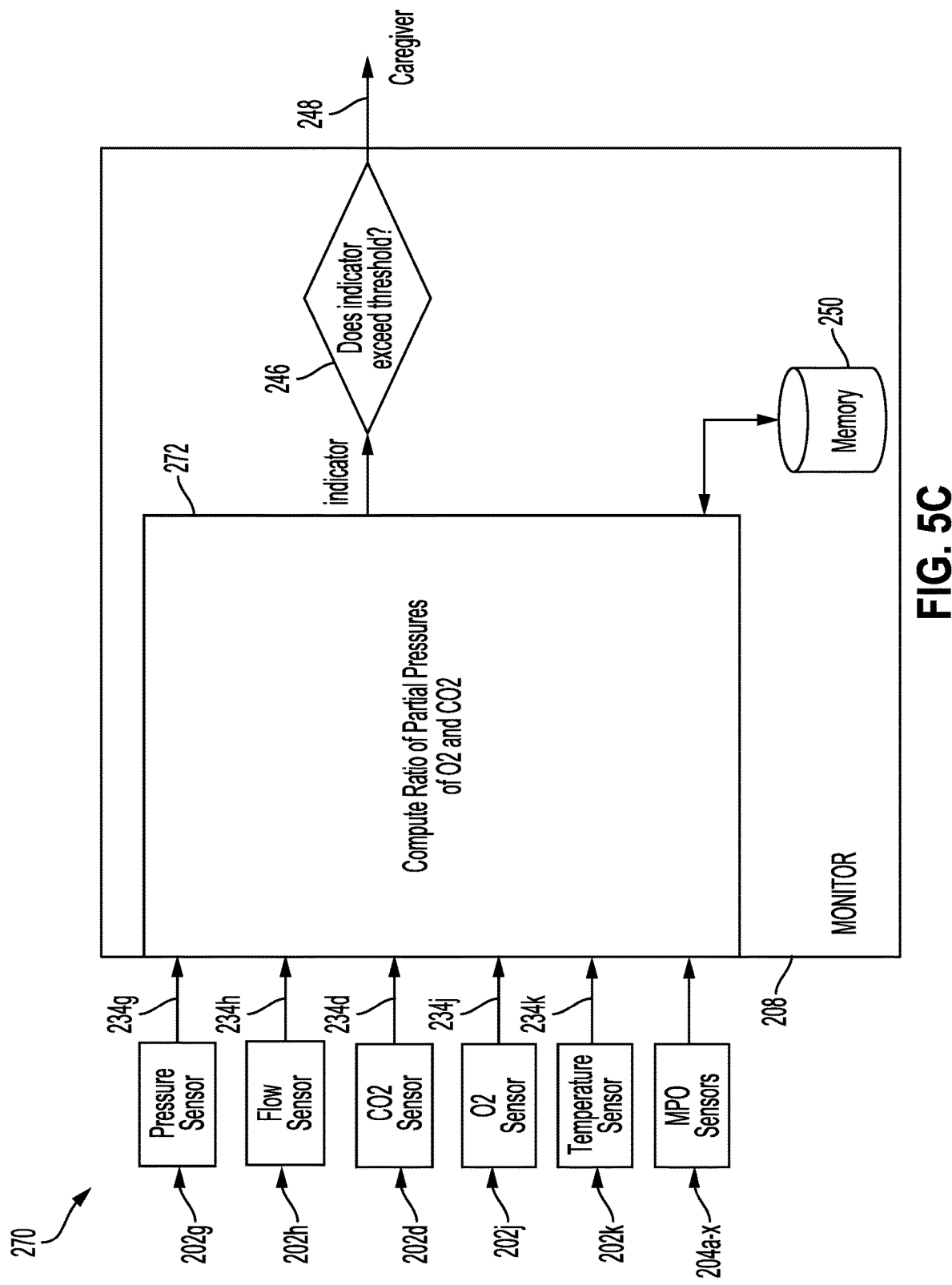
FIG. 5C is a block diagram illustrating an example algorithm for cardiopulmonary resuscitation (CPR) feedback, according to an example implementation.

FIG. 5C is a block diagram illustrating an example algorithm 270 for cardiopulmonary resuscitation (CPR) feedback, according to an example implementation. For example, a useful improvement in emergency patient care in the field is feedback as to whether CPR appears to provide forward blood flow through the pulmonary vasculature, and re-evaluation of (i) hand placement on the patient (on the chest, for example), (ii) depth of compression, (iii) rate of compression, or (iv) recoil. During cardiac arrest, the only means of transport of CO2 from the body tissue to the lungs is blood flow from the central veins through the pulmonary blood vessels. Therefore, measuring CO2 in expired gases gives an indication of pulmonary blood flow which is indicative of the effectiveness of CPR being delivered. However, ventilation during CPR is typically performed manually, and therefore the volume of ventilation is not closely controlled. Although CO2 partial pressure is proportional to the blood flow, the proportionality constant is dependent on volume of air exchanged. As such, additional information about ventilation may be needed to provide higher quality CO2 based CPR feedback.

The pressure sensor 202g is used to measure airway pressure (e.g., an indication of airflow pressure, for example, in a tube positioned within the trachea of the patient and used as an airway). The flow sensor 202h is used to measure rate of flow of gas in and out due to respiration (e.g., an indication of airflow in the tube). The CO2 sensor 202d is used to determine a partial pressure or fraction of CO2 (e.g., an indication of carbon dioxide inhaled or expelled by the patient) and an O2 sensor 202j is used to determine a partial pressure or fraction of O2 (e.g., an indication of oxygen inhaled or expelled by the patient). A temperature sensor 202k is optional as the airway temperature could be assumed.

Outputs of all sensors provided as 234g, 234h, 234d, 234j, 234k, or a proxy assumption as in the case of temperature, are used in combination with each other in determining the above feedback. For example, this group of sensors is being brought together in a particular way to determine partial pressures of O2 and CO2 in order to understand metabolism and pulmonary blood flow.

Using outputs from this grouping of sensors in FIG. 5C and the ideal gas law PV=nRT, the respiratory quotient (i.e., the number of moles of O2 inhaled vs. the number of moles of CO2 molecules exhaled out of the patient through the airway) can be calculated by the monitor 208 executing an algorithm 272 to measure oxygen consumption and respiration. The number of moles of CO2 exhaled is the indicator, which is then compared to the threshold 246. When the indicator fails to achieve the threshold 246, then the caregiver is alerted to re-evaluate CPR effectiveness. This output itself can, in turn, be combined with other indicators for CPR effectiveness described below to conclude that the patient is likely not to survive. The respiratory quotient itself has broader utility in understanding the metabolic state of the patient and may be a useful indicator for a wide variety of conditions such as chronic obstructive pulmonary disease and may potentially be a prognostic indicator for futility during resuscitation.

Figure 5D:
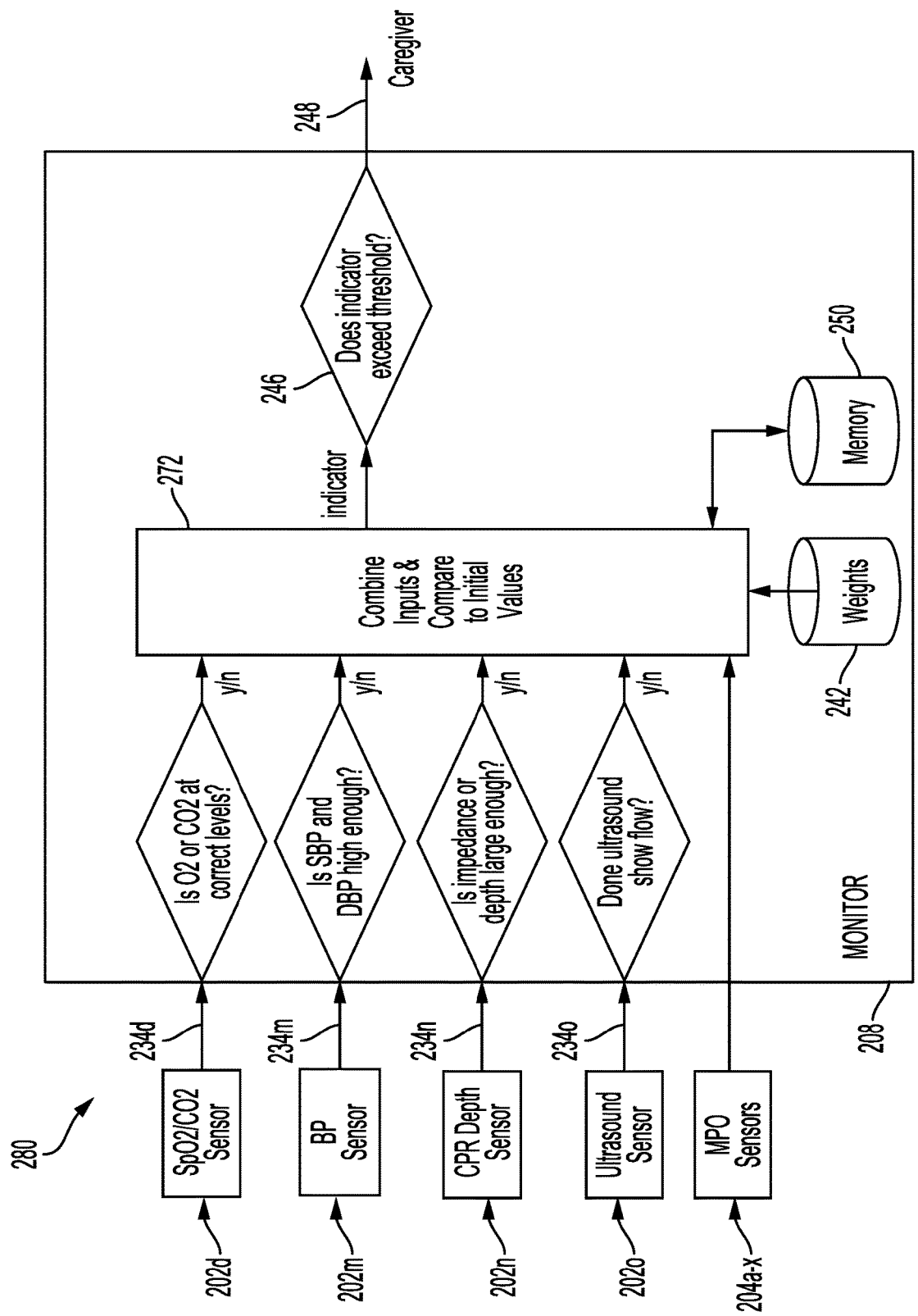
FIG. 5D is a block diagram illustrating another example algorithm for cardiopulmonary resuscitation (CPR) feedback, according to an example implementation.

FIG. 5D is a block diagram illustrating another example algorithm 280 for cardiopulmonary resuscitation (CPR) feedback, according to an example implementation. For example, another useful improvement in emergency patient care in the field is feedback as to (a) whether CPR appears to be moving a sufficient amount of oxygenated blood and (b) re-evaluation of hand placement on the chest, depth of compression, rate of compression, or recoil. This method utilizes a measurement indicative of oxygenation, a blood pressure waveform, a CPR depth quality metric, and a direct measure of volume flow in a blood vessel.

A sensor measuring airway CO2, such as in a capnograph, provides an indication of forward blood flow through the pulmonary vasculature. A sensor measuring the oxygenation of blood in cerebral tissue, rSO2, provides an indication of perfusion of the brain. A blood pressure (BP) sensor 202m can include one or more of a non-invasive blood pressure (NIBP) measurement made by a sphygmomanometer or oscillometric blood pressure cuff, a catheter inserted in an artery for a direct invasive pressure (IP) measurement, or a non-invasive measure of the BP waveform is used to determine an indication of a blood pressure of the patient. A CPR depth sensor 202n includes one or more of a direct depth measurement device using existing technology such as triaxial magnetic field induction (TFI) or accelerometers possibly augmented with magnetometers and gyros, or transthoracic impedance as measured from the impedance between ECG or defibrillation electrodes is used to determine an indication of a depth of compression applied during CPR. An ultrasound sensor 202o is measured by ultrasound transducers in potentially a patch form that is relatively low profile and sticks to the skin. Ultrasound is used to determine vessel area and flow profile over time including net flow.

Sensor parameters are first used individually to make an individual determination of CPR quality, and thus, outputs of the sensors 202d, 202m, 202n, and 202o are provided as waveforms 234d, 234m, 234n, and 234o to the monitor 208, which then determines if the measurement values fall within certain ranges. Suitable values of airway partial pressure of CO2 and rSO2 are indicators of CPR that is effective in moving blood through the lungs and to the brain. Ideally, blood pressure waveforms are obtained non-invasively or invasively have the advantage over a single number for systolic blood pressure (SBP) or diastolic blood pressure (DBP) in that the waveforms have timing information in them that can be correlated with other indicators to rule out extraneous or environmental motion that might give a false indication. Large fluctuations in transthoracic impedance may be indicators of good quality CPR on its own and can be corroborated with either BP waveforms or ultrasound flow waveforms to ensure that the impedance is fluctuating with blood flow. Ultrasound, being able to measure velocity as a function of time as well as the diameter or area of the vessel through which it flows, is able to calculate net flow. Good CPR is indicated when net flow is high enough.

Each of the outputs 234d, 234m, 234n, and 234o are converted to a yes/no/maybe indicator that can be combined in various ways as disclosed earlier in FIG. 5A and FIG. 5B. This includes the use of the MPO sensors 204a-x that are helpful with identifying false artifacts in each of these sensors due to motion. Even without the MPO sensors 204a-x, decision making performed by the monitor 208 executing the algorithm 272 can correlate ultrasound, impedance, and BP waveforms to ensure they are self-consistent to rule out artifacts thought to be effective CPR on one sensor when absent on other sensors. This also includes trending information leading to indicators that when not exceeded produce a prompt to the caregiver.

Figure 5E:
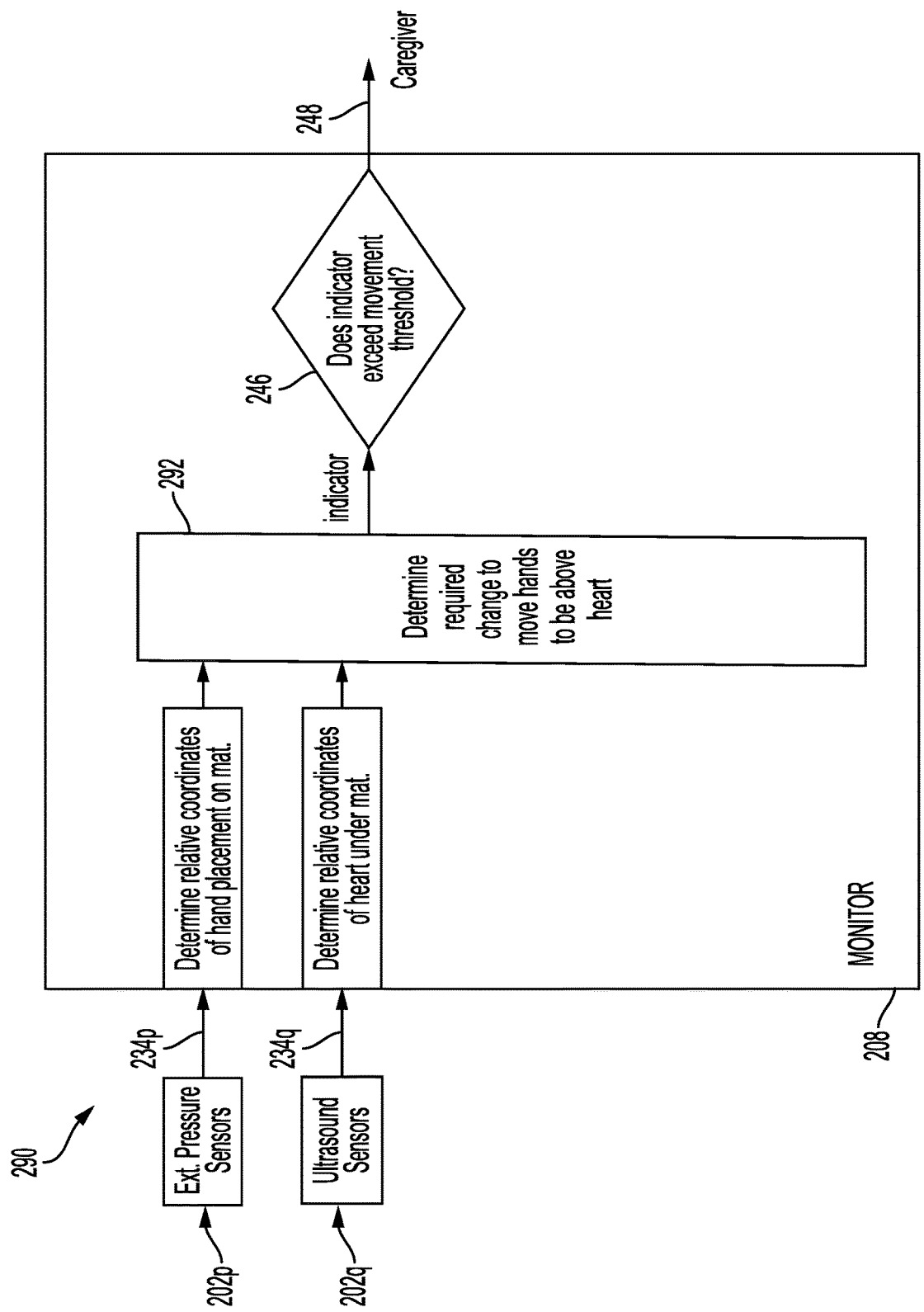
FIG. 5E is a block diagram illustrating another example algorithm for CPR feedback, according to an example implementation.

FIG. 5E is a block diagram illustrating another example algorithm 290 for CPR feedback, according to an example implementation. For example, another useful improvement in emergency patient care in the field is feedback as to whether hand placement for CPR needs to be adjusted; for example, to move further from the head or closer to the head. When the hands are high on the chest (too close to the head) flow out of the heart can be impeded due to compression of the left ventricular outflow tract. When hands are too low, the heart may not be compressed effectively and other internal injury might ensue.

External pressure sensors 202p are a plurality of sensors that can detect tactile pressure arranged in a mat. Each sensor indicates if it is being touched and a center to all the sensors touched is used to determine the position of the application of CPR force relative to the mat, and thus, the pressure sensors 202p indicate tactile pressure applied to a chest of a patient during CPR. External ultrasound sensors 202q arranged in the mat are used to identify where the heart is situated and perhaps the lower end of the sternum and the lungs, and thus, output an indication of a location of a heart of the patient. Where there is a window between the ribs, the heart may be identified by ultrasound as a pool of blood which is a volume of low reflectivity and its extent can be found. The sternum and lungs on the other hand are high reflectivity. With sufficient sensors detecting lungs below the surface, the heart below the surface, and the sternum and ribs at the surface, a map can be made of where the heart is under the mat. Additionally, or alternatively, the heart can be located by looking for myocardial walls which have higher ultrasound reflectivity or a combination of lower reflectivity pools of chambers of blood surrounded by high reflectivity myocardial walls.

Outputs 234p and 234q of the sensor are passed to the monitor 208, which executes an algorithm 292 to determine where the hands should be moved to if they are not close enough to the correct position. Options include closer to patient head or further away, primarily, and secondarily, patient left or right. An optimum displacement in these four directions are compared to the threshold 246 to determine if they are necessary, and if so, issue the prompt to the caregiver. Additionally or alternatively, the external pressure sensor 202p may have a built in indicators (lights, vibrating elements, etc.) that provide feedback to the care provider as to where to compress the chest. Additionally or alternatively, the built in indicators may also be used to provide CPR feedback for aspects such as compression rate, depth, and recoil by for example, changing color, flashing, or different vibration patterns.

It may be that CPR is being delivered by a mechanical CPR device (e.g., LUCAS). In this case the operator is prompted to adjust the piston position where force is applied.

Instead of external ultrasound, internal transesophageal ultrasound can be used to image the heart and determine if it is being appropriately compressed and released. Thus, the mapping function works from the inside looking out determining where the force appears to be applied looking at the heart and aorta and what is happening to them.

There is of course timing information in all these signals where motion as a function of time can be analyzed for a repetition frequency to determine if CPR rate is proper. Furthermore, ultrasound can be used to detect flow as well as depth of compression. Each of these can lead to prompts of pressing harder, softer, faster, slower, complete recoil, etc. (e.g., measured low flow or measured insufficient compression depth).

Figure 5F:
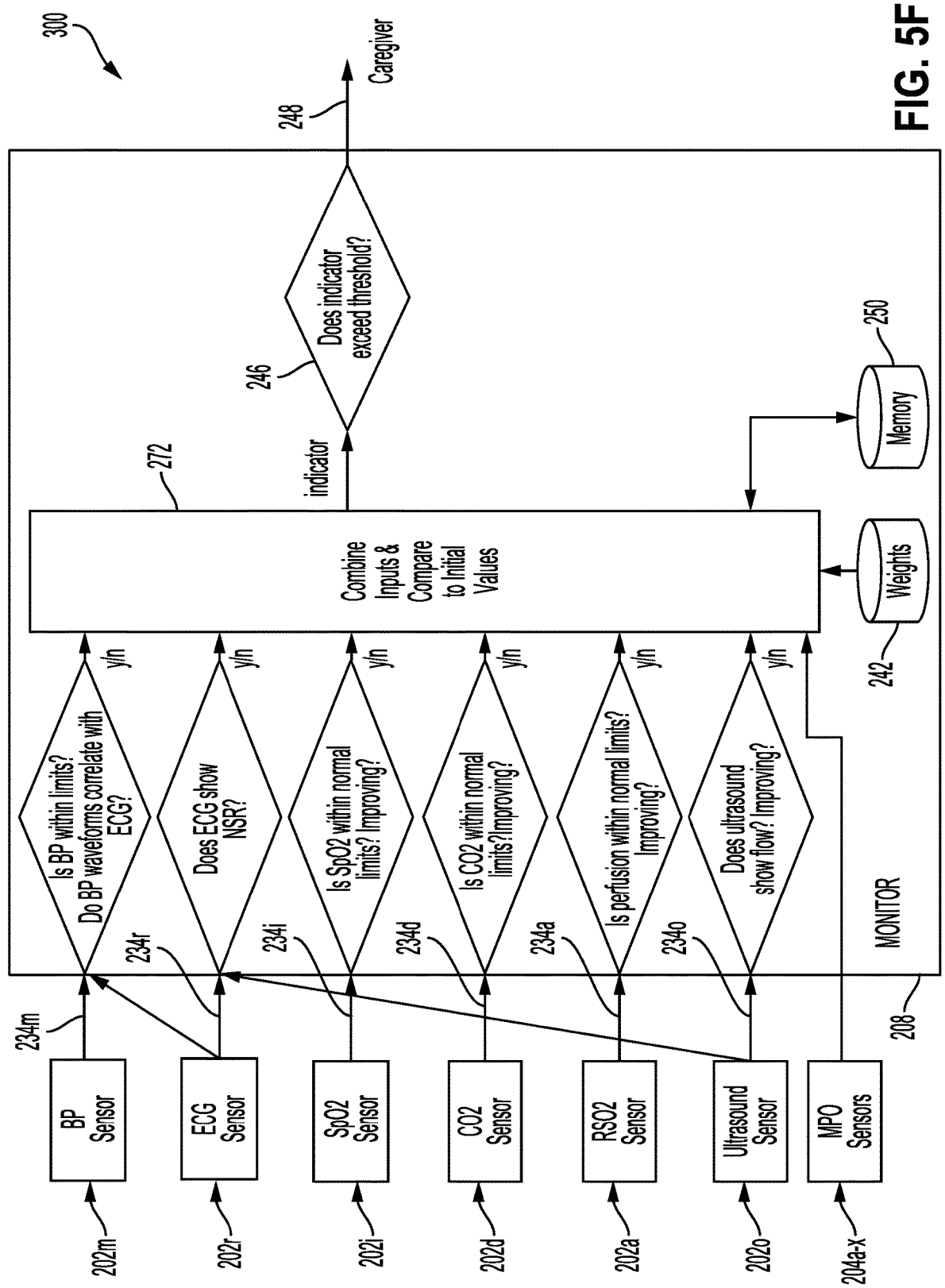
FIG. 5F is a block diagram illustrating another example algorithm for CPR feedback, according to an example implementation.

FIG. 5F is a block diagram illustrating another example algorithm 300 for CPR feedback, according to an example implementation. For example, another useful improvement in emergency patient care in the field is feedback to indicate (a) return of spontaneous circulation (ROSC) has occurred, or (b) presence of pulseless electrical activity (PEA). Although any one metric might be indicative of ROSC, the combination of metrics will provide a more reliable determination.

The blood pressure (BP) sensor 202m is one of a non-invasive blood pressure (NIBP) measurement made by a sphygmomanometer or oscillometric blood pressure cuff, a catheter inserted in an artery for a direct invasive pressure (IP) measurement, or a non-invasive measure of the BP waveform used to determine an indication of a blood pressure of the patient. The electrocardiogram (ECG) sensor 202r is any sensor of one or more leads measuring cardiac electrical signals. The SpO2 sensor 202i is measured by a plethysmograph of any available technology and determines an indication of oxygen saturation in the patient's blood. The CO2 sensor 202d is measured by a capnograph of any available technology, and determines an indication of carbon dioxide expelled by the patient. Tissue oxygenation is measured by the RSO2 sensor 202a. The ultrasound sensor 316f is made up of one or more transducers of piezoelectric material, CMUT, PMUT, or any other material that resonates in the MHz region and capable of transducing mechanical energy to electrical and electrical to mechanical, and determines an indication of a location of a heart of the patient, and in an alternative format, can detect blood flow or blood pressure.

In each case, the sensors provide corresponding sensor waveforms 234m, 234r, 234i, 234d, 234a, and 234o and output a metric indicative of what that sensor is measuring. The outputs of the sensors are provided to the monitor 208, which then determines if the measurement values falls within certain ranges and yields a logical answer of yes or no, or perhaps a maybe, which can be characterized by a 0 for "no," 1 for "yes," and a value in between for a "maybe." These logical answers may be modified based upon outputs of the MPO sensors 204a-x, for example, indicating an inordinate motion. For example, if there is motion relative to the ECG sensor 202r, that output data may be discarded by setting its weight to zero or "not applicable". This technique may also be used for the other sensors noted. A weighted sum of the logical answers can be combined in the algorithm 272, which outputs an indicator that is then compared to the threshold 246 to produce the feedback response 248.

Data over time may be stored in the memory 250 of the monitor 208. This allows the monitor 208 to perform a trending of each of the parameters over time. Given the temporal trends of these metrics used in the decisions, the question becomes one of whether the metric is sloping towards being within normal limits or away from them.

Weights can be set up to alert the operator of ROSC in any number of ways using a plurality of sensors such as any of the following exceeding the threshold 246 when: (a) ECG can be synchronized and correlated with blood pressure waveforms and ECG is NSR, (b) RSO2 rises and ECG is NSR, (c) ultrasound flow waveform is synchronized and correlated with ECG, (d) CO2 sufficiently improves when ECG is NSR, etc.

Furthermore, pulseless electrical activity can be reported when there is not flow as indicated by ultrasound and yet ECG shows organized cardiac electrical activity.

Figure 5G:
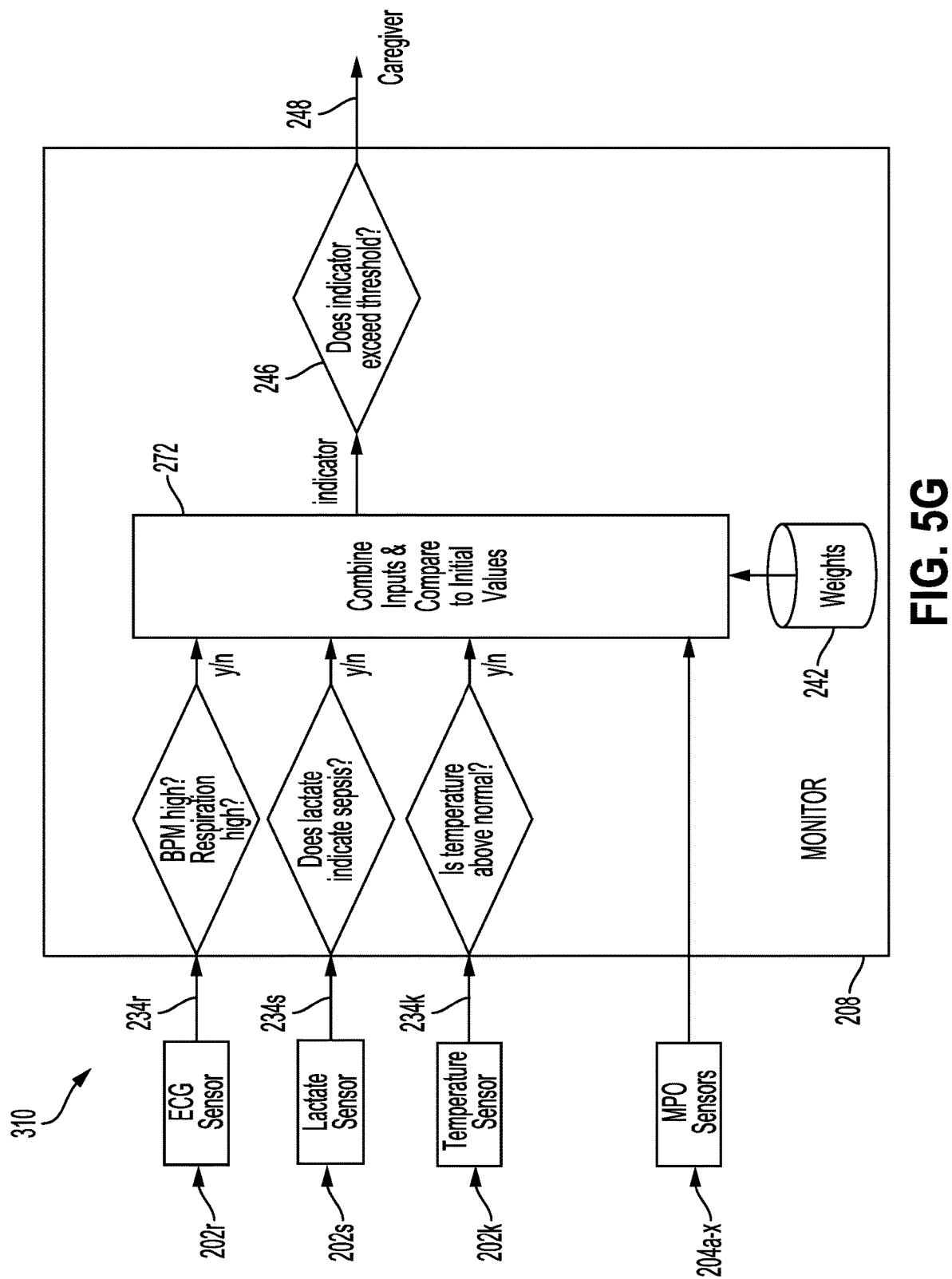
FIG. 5G is a block diagram illustrating another example algorithm for CPR feedback, according to an example implementation.

FIG. 5G is a block diagram illustrating another example algorithm 310 for CPR feedback, according to an example implementation. For example, another useful improvement in emergency patient care in the field is feedback to remind the caregiver to check for sepsis in the patient.

The ECG sensor 202r is any sensor of one or more leads measuring cardiac electrical signals. Respiratory motion also affects ECG lead signals and so respiration rate is able to be determined from them as well as the heart rate in beats per minute (BPM). Heart rate may also be obtained through SpO2 sensors or through blood pressure sensors. When therapy electrodes are applied, not only do they perform a one lead ECG but there is an impedance measurement. ECG leads may also allow measurement impedance as is done currently by various devices. The impedance measurement, whether from ECG leads or therapy electrodes, also can be processed for respiration rate. Respiration rate may also be obtained from MPO sensors placed on the patient's chest or stomach as well as capnography through various airway adjuncts such as a nasal cannula. A lactate sensor 202s is an output of a point of care blood work machine, and determines an indication of an analysis of blood of the patient. The point of care blood work machine may be able to process simultaneously or serially additional biomarkers besides lactate. The temperature sensor 202k detects patient temperature either by direct contact sensing or by a simplified version of a thermal camera measuring infrared emissions.

When therapy electrodes are applied, not only do they perform a one lead ECG but there is an impedance measurement. The impedance measurement also can be processed for respiration rate. A lactate sensor 202s is an output of a point of care blood work machine, and determines an indication of an analysis of blood of the patient. The temperature sensor 202k detects patient temperature either by direct contact sensing or by a simplified version of a thermal camera measuring infrared emissions.

In each case, the sensors provide corresponding sensor waveforms 234r, 234s, and 234k and output a metric indicative of what that sensor is measuring. The outputs of the sensors are provided to the monitor 208, which then determines if the measurement values falls within certain ranges and yields a logical answer of yes or no, or perhaps a maybe, which can be characterized by a 0 for "no," 1 for "yes," and a value in between for a "maybe." These logical answers may be modified based upon outputs of the MPO sensors 204a-x, for example, indicating an inordinate motion. For example, if there is motion relative to the ECG sensor 202r, that data may be discarded by setting its weight to zero or "not applicable". This technique may also be used for the other sensors noted. A weighted sum of the logical answers can be combined in the algorithm 272 from which an indicator is produced for comparison to the threshold 246 to produce the feedback response 248. The indicator threshold may also be modified depending upon which sensors are not applicable.

Within examples described herein, outputs of sensors are provided to the monitor 208, which then determines if the measurement values falls within certain ranges and can yield a logical answer of yes or no, or another Boolean output. In other examples, all the algorithms described herein can also include an approach of combining the outputs of the sensors via an analysis of the waveforms or multiple parameters (such as scalars, vectors, categories, matrices, vector fields, etc.). This can be useful, for example, because what might look like ROSC for a sensor independently may not be consistent with ROSC as two signals are analyzed simultaneously. For example, the ECG might show a rhythm consistent with a perfusing rhythm at a rate of 60 bpm, and in this case, the Boolean output for ECG is 1 for ROSC. Then the BP shows pulses occurring at a rate of 100 bpm, and so an analysis returns a Boolean output for BP of 1 for ROSC. But, in reality, such sensor outputs may be due to the patient being in pulseless electrical activity (PEA) and CPR was ongoing. If the rates from BP and ECG were compared, a false conclusion of ROSC may have been avoided because the rates do not match.

Figure 6:
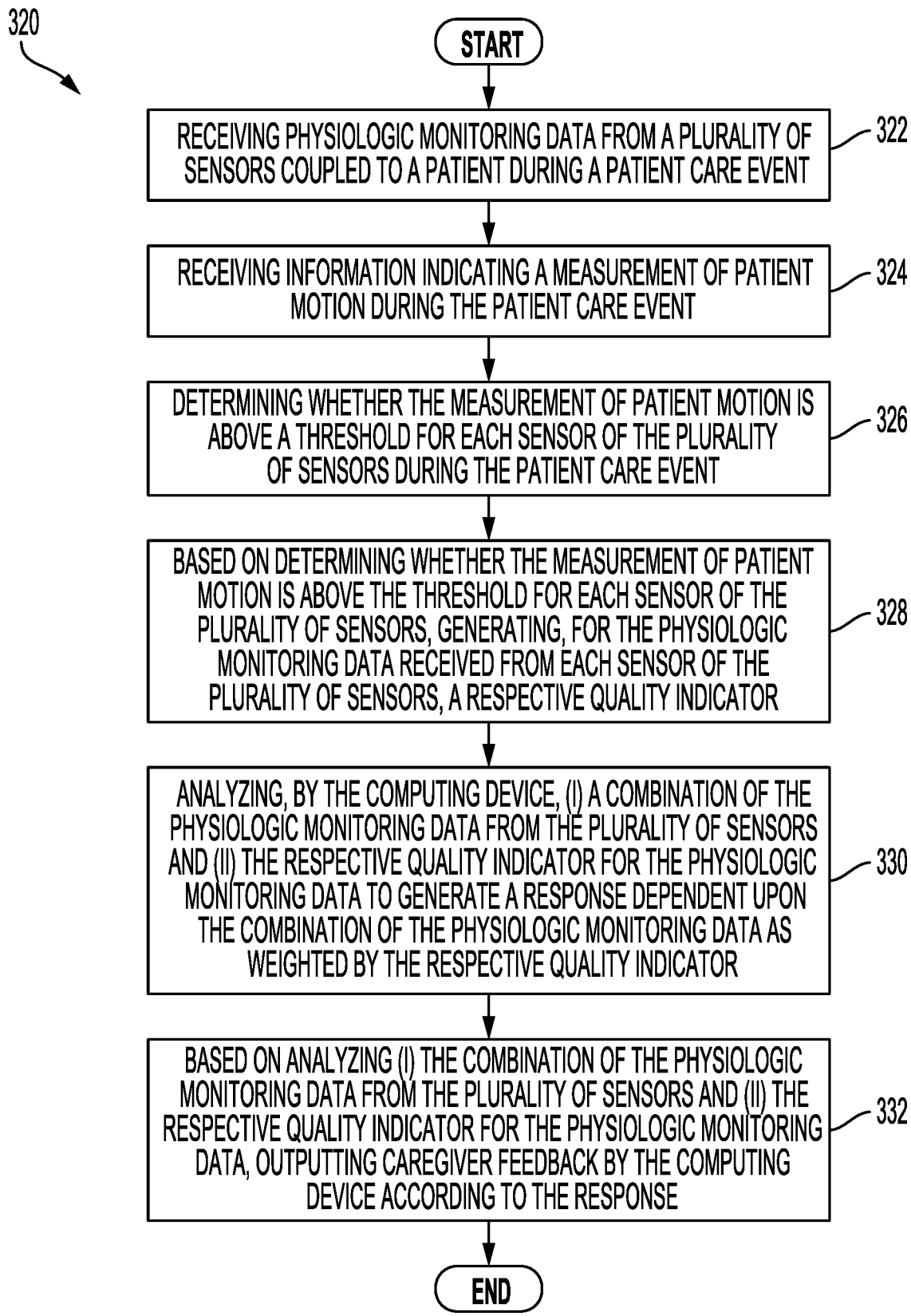
FIG. 6 shows a flowchart of another example of a method performed by a computing device executing instructions stored in data storage for providing patient parameter fusion and feedback, according to an example implementation.

FIG. 6 shows a flowchart of another example of a method 320 performed by a computing device executing instructions stored in data storage for providing patient parameter fusion and feedback, according to an example implementation. Method 320 shown in FIG. 6 presents an example of a method that could be used with the system 100 shown in FIG. 1 or with the computing device 102 shown in FIG. 1, for example. Further, devices or systems may be used or configured to perform logical functions presented in FIG. 6. In some instances, components of the devices and/or systems may be configured to perform the functions such that the components are actually configured and structured (with hardware and/or software) to enable such performance. In other examples, components of the devices and/or systems may be arranged to be adapted to, capable of, or suited for performing the functions, such as when operated in a specific manner. Method 320 may include one or more operations, functions, or actions as illustrated by one or more of blocks 322-332. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

It should be understood that for this and other processes and methods disclosed herein, flowcharts show functionality and operation of one possible implementation of present examples. In this regard, each block or portions of each block may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium may include non-transitory computer readable medium or memory, for example, such as computer-readable media that stores data for short periods of time like register memory, processor cache and Random Access Memory (RAM). The computer readable medium may also include non-transitory media, such as secondary or persistent long-term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In addition, each block or portions of each block in FIG. 6, and within other processes and methods disclosed herein, may represent circuitry that is wired to perform the specific logical functions in the process. Alternative implementations are included within the scope of the examples of the present disclosure in which functions may be executed out of order from that shown or discussed, including substantially concurrent or in reverse order, depending on the functionality involved, as would be understood by those reasonably skilled in the art.

At block 322, the method 320 includes receiving physiologic monitoring data from the plurality of sensors 202 coupled to a patient during a patient care event. In some examples, the computing device 102 may send a wireless signal to each of the plurality of sensors interrogating the plurality of sensors for data, and in response, receive the physiologic monitoring data from the plurality of sensors 202.

At block 324, the method 320 includes receiving information indicating a measurement of patient motion during the patient care event. In some example, this includes receiving, from the MPO sensors 204 integrated with each of the plurality of sensors 202, the information indicating the measurement of patient motion during the patient care event. In other examples, this includes receiving, from the MPO sensors 204 external from the plurality of sensors 202, the information indicating the measurement of patient motion during the patient care event.

At block 326, the method 320 includes determining whether the measurement of patient motion is above a threshold for each sensor of the plurality of sensors during the patient care event. The threshold for motion may vary based on the type of physiological monitoring data. The patient motion can also be measured and used as a continuous parameter or index, and could also variously include motion parameters such as magnitude, velocity, variability, and/or duration of motion measured. Each of these motion parameters can be a basis for determining whether the measurement of patient motion is above a threshold at any instance, or above a threshold for an amount of time during the duration of motion measured.

At block 328, the method 320 includes based on determining whether the measurement of patient motion is above the threshold for each sensor of the plurality of sensors, generating, for the physiological monitoring data received from each sensor of the plurality of sensors, a respective quality indicator. The respective quality indicator may be a weight to apply to the output of the sensor during further processing.

In one example, block 328 includes receiving information indicative of a temperature at the plurality of sensors, and based on determining whether the temperature at the plurality of sensors is above the threshold for each sensor of the plurality of sensors, generating, for the physiological monitoring data received from each sensor of the plurality of sensors, the respective quality indicator. In another example, block 328 includes receiving information indicative of ambient light at the plurality of sensors, and based on determining whether ambient light at the plurality of sensors is above the threshold for each sensor of the plurality of sensors, generating, for the physiological monitoring data received from each sensor of the plurality of sensors, the respective quality indicator.

In particular, in all the above example algorithms where perfusion is measured, such as with SpO2 or RSO2, not only are MPO sensors helpful in qualifying validity of these physiological monitoring data, but also temperature at the sensor as well as ambient light. Temperature can be important as blood perfusion provides tissue heat. If there is little or no perfusion to some tissue, the tissue will have a temperature closer to that of the environment compared to perfused tissue. Furthermore, since SpO2, RSO2, CO2, as well as any other metrics using light as a sensing mechanism can be corrupted by ambient light fluctuations, another sensor for measuring ambient light may be incorporated into the vital sign sensor for the purpose of qualifying the signal or even for subtracting out the ambient variation from the signal.

In yet further examples, block 328 further includes generating a confidence factor based upon the amount that the measurement of patient motion is above the threshold for each sensor of the plurality of sensors. In all the above example algorithms, the feedback can be issued with a confidence factor, for example, based upon a fractional amount the indicator exceeds the selected threshold. The confidence factor could be conveyed by a change of color, the size of the font, a graphic that attends it.

Moreover, in other examples, block 328 can further include based on determining whether the measurement of patient motion is above the threshold for each sensor of the plurality of sensors, qualifying a validity of the physiological monitoring data, and when any of the physiological monitoring data are invalid, removing the respective physiological monitoring data from further analyzing.

At block 330, the method 320 includes analyzing, by the computing device, (i) a combination of the physiological monitoring data from the plurality of sensors and (ii) the respective quality indicator for the physiological monitoring data to generate a response dependent upon the combination of the physiological monitoring data as weighted by the respective quality indicator. Example specific analysis are described above with respect to FIGS. 5A-5G.

In further examples, block 320 includes determining an expected correlation between multiple of the physiological monitoring data, and when a respective expected correlation is lacking, triggering an error of one of the physiological monitoring data.

At block 332, the method 320 includes based on analyzing (i) the combination of the physiological monitoring data from the plurality of sensors and (ii) the respective quality indicator for the physiological monitoring data, outputting caregiver feedback by the computing device according to the response. Example caregiver feedback are described above with respect to FIGS. 5A-5G.

In further examples, the method 320 can also include determining, at a timestamp, a substantive change in a physiological monitoring data from one of the plurality of sensors 202, identifying whether the measurement of patient motion is above the threshold at the timestamp to determine if there was a position change of the patient, and based on determining that there was the position change of the patient, outputting the caregiver feedback as indicative of the physiological monitoring data from the one of the plurality of sensors 202 being low quality at the timestamp. In this manner, the output of the sensor is marked as low quality due to corruption of the sensing by the sensors as a result of patient motion.

In yet further examples, the method 320 can also include determining, at a timestamp, a substantive change in a physiological monitoring data from one of the plurality of sensors 202, identifying whether the measurement of patient motion is above the threshold at the timestamp to determine if there was a position change of the patient, and based on determining that there was the position change of the patient, discarding or ignoring the physiological monitoring data that occurred at the timestamp. Still further, the method 320 can also include determining, at a timestamp, a substantive change in a physiological monitoring data from one of the plurality of sensors, identifying whether the measurement of patient motion is above the threshold at the timestamp to determine if there was a position change of the patient, and based on determining that there was the position change of the patient resulting in a corrupted physiological monitoring data, pausing the caregiver feedback until the patient motion abates. In these examples, the measurements are discarded or feedback is paused due to corruption of the sensing by the sensors as a result of patient motion.

In another example, the method 320 can also include running a diagnosis algorithm to diagnose a condition of the patient, determining a missing input to the diagnosis algorithm, and outputting a recommendation, by the computing device, for another sensor to be applied to the patient for collection of one or more additional physiological monitoring data. For example, in all the above example algorithms, feedback to the operator could also include recommendation for another sensor to be applied. The algorithms may be augmented that if the indicator is close to the threshold, for example on a fractional basis, that the monitor 208 would review the weights and ensure that the sensors for the top three weighted metrics are applied. If not, then a recommendation to the caregiver would be issued to add that sensor. Additionally or alternatively, the caregiver can choose not to add one or more recommended sensors and continue with the analysis; if the caregiver so chooses, the algorithm may still provide an interpretation but with feedback that makes clear to user the likelihood of degraded diagnostic accuracy due to insufficient inputs.

In another example, as described above with respect to FIG. 5A, the method 320 can also include receiving, from a camera, images indicative of placement of a tube for intubation in the patient, receiving, from a carbon dioxide detector, an indication of carbon dioxide expelled by the patient, receiving, from a microphone, an indication of sounds in the tube, receiving, from a gas detector, an indication of presence of gases of interest (such as CO2 partial pressure) in the tube, and based on a combination of the physiological monitoring data from the plurality of sensors and the respective quality indicator for the physiological monitoring data, outputting the caregiver feedback by the computing device indicative of whether the tube is properly placed in the patient and whether the tube has moved out of place since installation. In such examples, comparisons of a first set of the physiological monitoring data when the tube for intubation was determined visually by a caregiver as correct to a second set of the physiological monitoring data received at a later time can be made, and the caregiver feedback can be output by the computing device indicative of whether the tube has moved out of place since installation based on a change in the first set of the physiological monitoring data to the second set of the physiological monitoring data.

In another example, as described above with respect to FIG. 5B, the method 320 can also include receiving, from a pressure sensor, an indication of pressure in a tube for intubation in the patient, receiving, from an air flow sensor, an indication of airflow in the tube, receiving, from a pulse oximetry sensor, a measure of exhaled oxygenation in the patient, and based on a combination of the physiological monitoring data from the plurality of sensors and the respective quality indicator for the physiological monitoring data, outputting the caregiver feedback by the computing device indicative of one or more of: whether an airway of the patient is over pressurized, whether a volume of air is too high and patient oxygenation is too high, whether the volume of air is too low and the patient oxygenation is inadequate, and spontaneous breathing.

In another example, as described above with respect to FIG. 5C, the method 320 can also include receiving, from a pressure sensor, an indication of pressure in a tube for intubation in the patient, receiving, from an air flow sensor, an indication of airflow in the tube, receiving, from a carbon dioxide sensor, an indication of carbon dioxide expelled by the patient, receiving, from an oxygen sensor, an indication of oxygen inhaled by the patient, and based on a combination of the physiological monitoring data from the plurality of sensors and the respective quality indicator for the physiological monitoring data, outputting the caregiver feedback by the computing device indicative of one or more of: whether cardiopulmonary resuscitation (CPR) appears to cause forward blood flow, and re-evaluation of (i) hand placement on the patient, (ii) depth of compression, (iii) rate of compression, or (iv) recoil.

In another example, as described above with respect to FIG. 5D, the method 320 can also include receiving, from a CO2 sensor, an indication of forward blood flow through the pulmonary vasculature, receiving, from a blood pressure sensor, an indication of a blood pressure of the patient, receiving, from a depth sensor, an indication of a depth of compression applied during cardiopulmonary resuscitation (CPR), receiving, from an ultrasound sensor, an indication of vessel area and flow profile over time, and based on a combination of the physiological monitoring data from the plurality of sensors and the respective quality indicator for the physiological monitoring data, outputting the caregiver feedback by the computing device indicative of one or more of: whether CPR appears to be moving a sufficient amount of blood, and re-evaluation of (i) hand placement on the patient, (ii) depth of compression, (iii) rate of compression, or (iv) recoil.

In another example, as described above with respect to FIG. 5E, the method 320 can also include receiving, from external pressure sensors, tactile pressure applied to a chest of a patient during cardiopulmonary resuscitation (CPR), receiving, from external ultrasound sensors, an indication of a location of a heart of the patient, and based on a combination of the physiological monitoring data from the plurality of sensors and the respective quality indicator for the physiological monitoring data, outputting the caregiver feedback by the computing device indicative of whether hand placement for CPR needs to be adjusted.

In another example, as described above with respect to FIG. 5F, the method 320 can also include receiving, from a blood pressure sensor, an indication of a blood pressure of the patient, receiving, from an electrocardiogram (ECG) sensor, one or more cardiac electrical signals, receiving, from an oxygen sensor, an indication of oxygen inhaled and exhaled by the patient, receiving, from a carbon dioxide sensor, an indication of carbon dioxide expelled by the patient, receiving, from external ultrasound sensors, an indication of a location of a heart of the patient, and based on a combination of the physiological monitoring data from the plurality of sensors and the respective quality indicator for the physiological monitoring data, outputting the caregiver feedback by the computing device indicative of one of return of spontaneous circulation (ROSC) or pulseless electrical activity (PEA).

In another example, as described above with respect to FIG. 5G, the method 320 can also include receiving, from an electrocardiogram (ECG) sensor, one or more cardiac electrical signals, receiving, from a lactate sensor, an indication of an analysis of blood of the patient, receiving, from a temperature sensor, an indication of patient temperature, and based on a combination of the physiological monitoring data from the plurality of sensors and the respective quality indicator for the physiological monitoring data, outputting the caregiver feedback by the computing device indicative of a reminder to check for sepsis in the patient.

Figure 7:
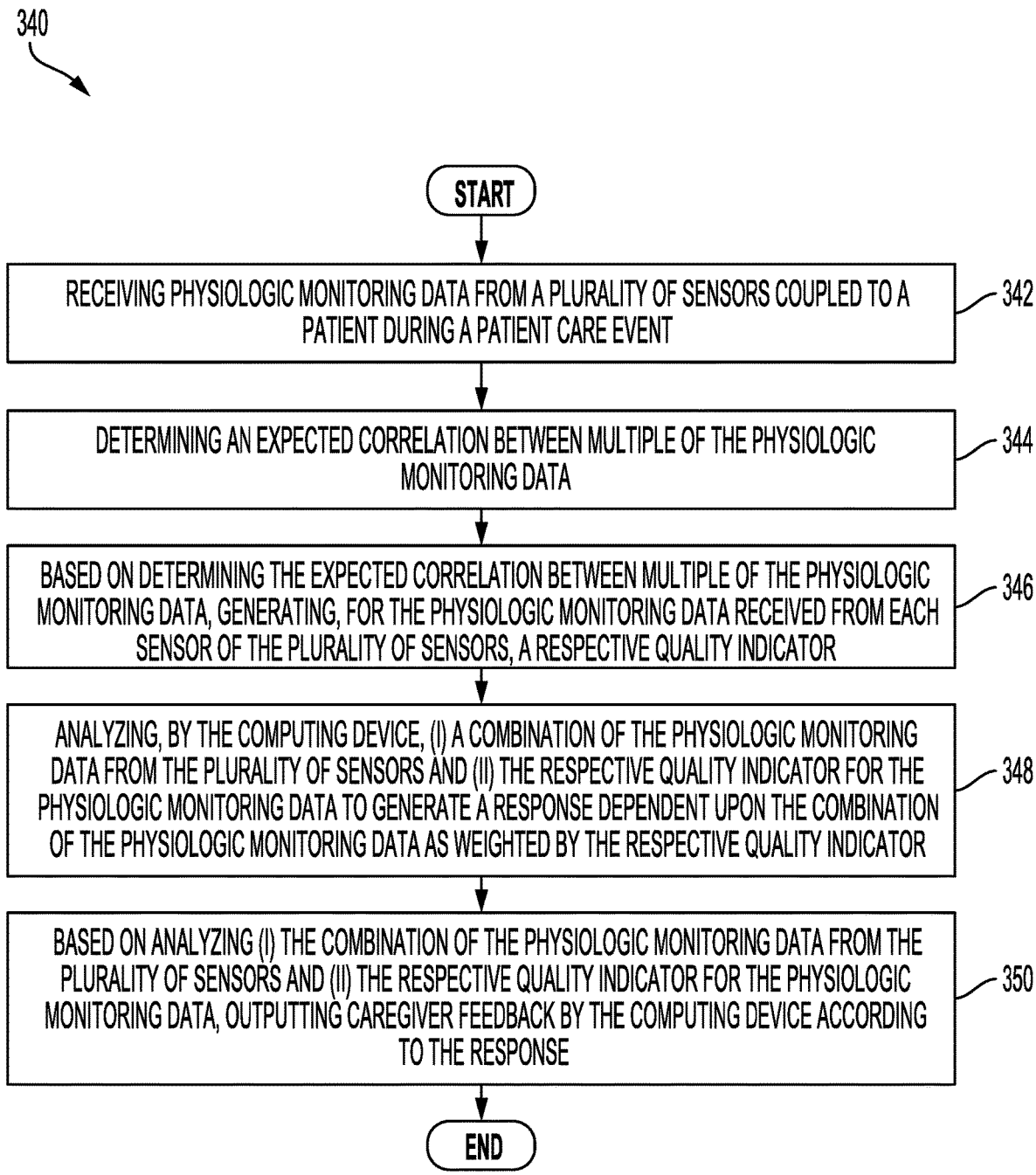
FIG. 7 shows a flowchart of another example of a method performed by a computing device executing instructions stored in data storage for providing patient parameter fusion and feedback, according to an example implementation.

FIG. 7 shows a flowchart of another example of a method 340 performed by a computing device executing instructions stored in data storage for providing patient parameter fusion and feedback, according to an example implementation. Method 340 shown in FIG. 7 presents an example of a method that could be used with the system 100 shown in FIG. 1 or with the computing device 102 shown in FIG. 1, for example. Further, devices or systems may be used or configured to perform logical functions presented in FIG. 7.

At block 342, the method 340 includes receiving physiological monitoring data from a plurality of sensors coupled to a patient during a patient care event. At block 344, the method 340 includes determining an expected correlation between multiple of the physiological monitoring data or sensor waveforms. At block 346, the method 340 includes based on determining the expected correlation between multiple of the physiological monitoring data or sensor waveforms, generating, for the physiological monitoring data or sensor waveforms received from each sensor of the plurality of sensors, a respective quality indicator. At block 348, the method 340 includes analyzing, by the computing device, (i) a combination of the physiological monitoring data or sensor waveforms from the plurality of sensors and (ii) the respective quality indicator for the physiological monitoring data or sensor waveforms to generate a response dependent upon the combination of the physiological monitoring data or sensor waveforms as weighted by the respective quality indicator. At block 350, the method 340 includes based on analyzing (i) the combination of the physiological monitoring data or sensor waveforms from the plurality of sensors and (ii) the respective quality indicator for the physiological monitoring data or sensor waveforms, outputting caregiver feedback by the computing device according to the response.

In the above example algorithms (especially when MPO sensors are not present), when a correlation is not present as expected between multiple signals, that triggers an error of one of the signals. For example, in a first group, flow variations detected by ultrasound should be correlated with pressure variations detected by continuous NIBP or IP which, in turn, should be correlated to variations in ECG. Whenever any pair of these do not agree in the existence of a rate of variation or a relative timing of the variation and one is definitely showing a reasonable waveform, then the caregiver is alerted to check the other sensor. The method 340 would generate a quality indicator for the specific sensor as low, which would trigger the error indicator output to the caregiver.

As a second example, in a second group of sensors, SpO2, RSO2, and CO2 should be within limits. Whenever any pair of these do not agree and one is definitely showing a reasonable waveform, then the caregiver may be alerted to check the other sensor. RSO2 may be measured with two sensors applied to the left and right surface of the forehead, and the readings from the two sensors may be processed to assess signal quality, and the caregiver may be alerted to check one or both sensors.

In a third example, if there is only one sensor in the first group and one sensor in the second group, say ECG and SpO2, and SpO2 is showing good oxygenation of the blood, but ECG does not show a corresponding rhythm, then the caregiver might be alerted to check ECG.

Figure 8:
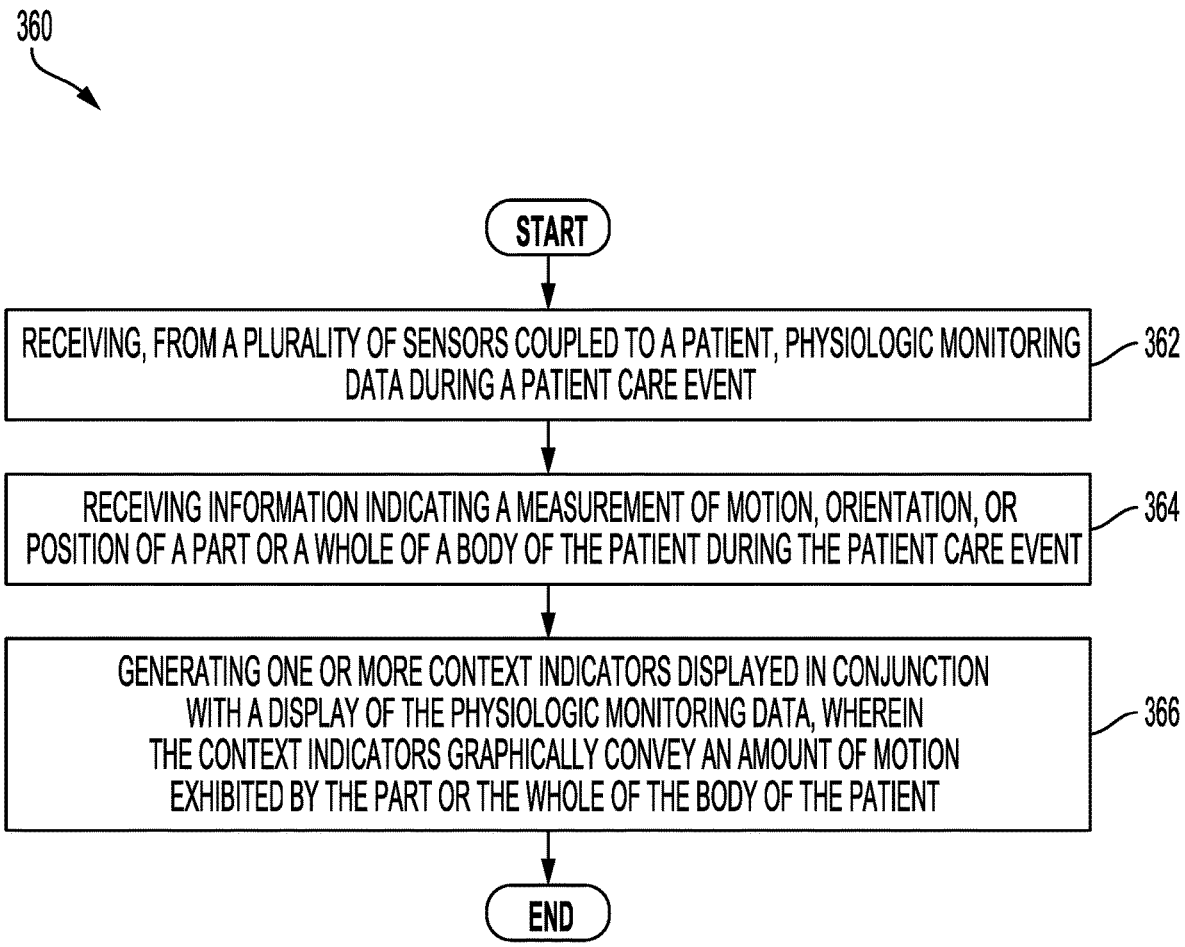
FIG. 8 shows a flowchart of another example of a method performed by a computing device executing instructions stored in data storage for providing patient parameter fusion and feedback, according to an example implementation.

FIG. 8 shows a flowchart of another example of a method 360 performed by a computing device executing instructions stored in data storage for providing patient parameter fusion and feedback, according to an example implementation. Method 360 shown in FIG. 8 presents an example of a method that could be used with the system 100 shown in FIG. 1 or with the computing device 102 shown in FIG. 1, for example. Further, devices or systems may be used or configured to perform logical functions presented in FIG. 8.

At block 362, the method 360 includes receiving, from a plurality of sensors coupled to a patient, physiologic monitoring data during a patient care event.

At block 364, the method 360 includes receiving information indicating a measurement of motion, orientation, or position of a part or a whole of a body of the patient during the patient care event.

At block 366, the method 360 includes generating one or more context indicators displayed in conjunction with a display of the physiologic monitoring data, wherein the context indicators graphically convey an amount of motion exhibited by the part or the whole of the body of the patient.

In one example, the context indicators graphically convey the orientation of the position of the part or the whole of the body of the patient. In other examples, the context indicators provide one or more snapshot indications of patient motion or position. Still further, in another example, the context indicators to provide a continuous indication of patient motion or position.

Thus, via the motion, position, and/or orientation sensors, the monitor 208 may determine whether the patient was still (e.g., calm or unconscious), mildly moving part or all of their body, or vigorously moving part or all of their body (e.g., in extreme distress or agitation). This is useful context related to the state of the patient at the time the physiologic measurements were being made. Additionally, the motion, position, and/or orientation sensors could be used to reconstruct the position in which a patient was placed or situated at any given time, or over any given period of time by receiving the motion data from the MPO sensors that are also associated with specific placement positions on the patient. This position information can be used to interpret physiological monitoring data, vital signs, or changes in physiological monitoring data or vital signs.

In one example, historically "orthostatic vital signs" have been measured in a number of different types of patients receiving emergency medical care, and heart rate (or pulse rate) and blood pressure are sequentially measured while the patient is supine, then sitting, then standing. Observation of large increases in heart/pulse rate, and/or large decreases in blood pressure, can help inform the assessment, diagnosis, and/or care of the patient. In another example, patient positioning can significantly affect a patient's physiology, and is actually a treatment for several emergency medical conditions. Specifically, patients in many types of respiratory distress have a significantly harder time breathing in a supine position than in a sitting-upright position, and for this reason, emergency medical providers should position the patients in a sitting-upright position. Data from motion/position/orientation sensors could help quality improvement personnel conduct post-event review of a patient care event and identify whether best practices of patient positioning were adhered to during the patient care event. Similarly, the position a patient is placed in can impact the ease or difficulty of intubation, and thus, such patient position data could provide valuable context (e.g. for the quality improvement personnel conducting post-event review) for interpreting the efficacy of an intubation attempt and for interpreting the physiologic measurement changes that occurred during an intubation attempt.

The systems and methods described herein are very beneficial to provider better and more accurate feedback to the caregiver. The systems and methods provide a solution to improve feedback with respect to intubation, CPR, patient monitoring, etc., in which a patient is connected to a ventilator, CPR, blood pressure sensors, patient monitor, etc., and rather than providing individual feedback of each sensor independently, outputs of all sensors are analyzed to provide a more intelligent output. Generally, outputs of one sensor cannot give a full picture of whether intubation is being performed properly, for example, and thus, the parameter fusion algorithms provide a more accurate analysis for improved feedback.

Implementations of this disclosure provide technological improvements that are particular to computer technology, for example, those concerning analysis of sensor outputs particular to a specific therapy being provided. Computer-specific technological problems, such as improving trustworthiness of outputs of sensors, can be solved using technical solutions described herein. When outputs of two sensors are utilized in a therapy algorithm, and motion is detected that may corrupt one of the outputs, a confidence or quality metric can be determined and associated with the sensor output. Further, a time alignment of sensor outputs can be analyzed to determine truths or confidence of measurements.

As a result, implementations of this disclosure can thus introduce new and efficient improvements in the ways in which outputs of sensors are processed to determine changes or modifications to therapy to provide to a patient.

By the term "substantially" and "about" used herein, it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide.

Different examples of the system(s), device(s), and method(s) disclosed herein include a variety of components, features, and functionalities. It should be understood that the various examples of the system(s), device(s), and method(s) disclosed herein may include any of the components, features, and functionalities of any of the other examples of the system(s), device(s), and method(s) disclosed herein in any combination or any sub-combination, and all of such possibilities are intended to be within the scope of the disclosure.

The description of the different advantageous arrangements has been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to best explain the principles of the examples, the practical application, and to enable others of ordinary skill in the art to understand the disclosure for various examples with various modifications as are suited to the particular use contemplated.

What is claimed is:

1. A method performed by a computing device executing instructions stored in data storage, the method comprising:
    receiving physiologic monitoring data from a plurality of sensors coupled to a patient during a patient care event, wherein each of the plurality of sensors has an associated motion, position, and/or orientation (MPO) sensor external from the plurality of sensors and configured to output information indicating a measurement of patient motion during the patient care event;
    based on the physiologic monitoring data indicating a substantive change, interrogating the MPO sensor associated with a particular one of the plurality of sensors outputting the physiologic monitoring data indicating the substantive change;
    receiving the information indicating the measurement of patient motion during the patient care event from the interrogated MPO sensor;
    determining whether the measurement of patient motion is above a threshold for the particular one of the plurality of sensors during the patient care event;
    based on determining whether the measurement of patient motion is above the threshold for the particular one of the plurality of sensors, generating, for the physiologic monitoring data received from each sensor of the plurality of sensors, a respective quality indicator;
    analyzing, by the computing device, (i) a combination of the physiologic monitoring data from the plurality of sensors and (ii) the respective quality indicator for the physiologic monitoring data to generate a response dependent upon the combination of the physiologic monitoring data as weighted by the respective quality indicator; and
    based on analyzing (i) the combination of the physiologic monitoring data from the plurality of sensors and (ii) the respective quality indicator for the physiologic monitoring data, outputting caregiver feedback by the computing device according to the response.

2. The method of claim 1, further comprising:
    receiving information indicative of a temperature at the plurality of sensors; and
    based on determining whether the temperature at the plurality of sensors is above the threshold for each sensor of the plurality of sensors, generating, for the physiologic monitoring data received from each sensor of the plurality of sensors, the respective quality indicator.

3. The method of claim 1, further comprising:
    receiving information indicative of ambient light at the plurality of sensors; and
    based on determining whether ambient light at the plurality of sensors is above the threshold for each sensor of the plurality of sensors, generating, for the physiologic monitoring data received from each sensor of the plurality of sensors, the respective quality indicator.

4. The method of claim 1, further comprising:
sending, by the computing device, a wireless signal to each of the plurality of sensors interrogating the plurality of sensors for data; and
in response, receiving the physiologic monitoring data from the plurality of sensors.

5. The method of claim 1, further comprising:
determining, at a timestamp, the substantive change in a physiologic monitoring data from one of the plurality of sensors;
identifying whether the measurement of patient motion is above the threshold at the timestamp to determine if there was a position change of the patient; and
based on determining that there was the position change of the patient, outputting the caregiver feedback as indicative of the physiologic monitoring data from the one of the plurality of sensors being low quality at the timestamp.

6. The method of claim 1, further comprising:
determining, at a timestamp, the substantive change in a physiologic monitoring data from one of the plurality of sensors;
identifying whether the measurement of patient motion is above the threshold at the timestamp to determine if there was a position change of the patient; and
based on determining that there was the position change of the patient, discarding or ignoring the physiologic monitoring data that occurred at the timestamp.

7. The method of claim 1, further comprising:
determining, at a timestamp, the substantive change in a physiologic monitoring data from one of the plurality of sensors;
identifying whether the measurement of patient motion is above the threshold at the timestamp to determine if there was a position change of the patient; and
based on determining that there was the position change of the patient resulting in corrupted physiologic monitoring data, pausing the caregiver feedback until the patient motion abates.

8. The method of claim 1, wherein said analyzing comprises running a diagnosis algorithm to diagnose a condition of the patient, and
wherein outputting the caregiver feedback comprises outputting a recommendation, by the computing device, for another sensor to be applied to the patient for collection of one or more additional physiologic monitoring data.

9. The method of claim 1, further comprising:
determining an amount that the measurement of patient motion is above the threshold for each sensor of the plurality of sensors; and
wherein generating the respective quality indicator comprises further generating a confidence factor based upon the amount that the measurement of patient motion is above the threshold for each sensor of the plurality of sensors.

10. The method of claim 1, wherein said analyzing comprises determining an expected correlation between multiple of the physiologic monitoring data; and
the method further comprises:
when a respective expected correlation is lacking, triggering an error of one of the physiologic monitoring data.

11. The method of claim 1, further comprising:
based on determining whether the measurement of patient motion is above the threshold for each sensor of the plurality of sensors, qualifying a validity of the physiologic monitoring data; and
when any of the physiologic monitoring data are invalid, removing the respective physiologic monitoring data from said analyzing.

12. The method of claim 1, wherein receiving the physiologic monitoring data comprises:
receiving, from a camera, images indicative of placement of a tube for intubation in the patient;
receiving, from a carbon dioxide detector, an indication of carbon dioxide expelled by the patient;
receiving, from a microphone, an indication of sounds in the tube; and
receiving, from a gas detector, an indication of presence of gases in the tube; and
the method further comprising:
based on a combination of the physiologic monitoring data from the plurality of sensors and the respective quality indicator for the physiologic monitoring data, outputting the caregiver feedback by the computing device indicative of whether the tube is properly placed in the patient and whether the tube has moved out of place since installation.

13. The method of claim 12, further comprising:
comparing a first set of the physiologic monitoring data when the tube for intubation was determined visually by a caregiver as correct to a second set of the physiologic monitoring data received at a later time; and
outputting the caregiver feedback by the computing device indicative of whether the tube has moved out of place since installation based on a change in the first set of the physiologic monitoring data to the second set of the physiologic monitoring data.

14. The method of claim 1, wherein receiving the physiologic monitoring data comprises:
receiving, from a pressure sensor, an indication of airflow pressure in a tube for intubation in the patient;
receiving, from an air flow sensor, an indication of airflow in the tube; and
receiving, from a pulse oximetry sensor, a measure of blood oxygenation in the patient;
the method further comprising:
based on a combination of the physiologic monitoring data from the plurality of sensors and the respective quality indicator for the physiologic monitoring data, outputting the caregiver feedback by the computing device indicative of one or more of: whether an airway of the patient is over pressurized, whether a volume of air is too high and patient oxygenation is too high, whether the volume of air is too low and the patient oxygenation is inadequate, and spontaneous breathing.

15. The method of claim 1, wherein receiving the physiologic monitoring data comprises:
receiving, from a pressure sensor, an indication of airflow pressure in a tube for intubation in the patient;
receiving, from an air flow sensor, an indication of airflow in the tube;
receiving, from a carbon dioxide sensor, an indication of carbon dioxide expelled by the patient; and
receiving, from an oxygen sensor, an indication of oxygen inhaled by the patient;
the method further comprising:
based on a combination of the physiologic monitoring data from the plurality of sensors and the respective quality indicator for the physiologic monitoring data, outputting the caregiver feedback by the computing device indicative of one or more of: whether cardiopulmonary resuscitation (CPR) appears to sustain targeted or expected levels of expired carbon dioxide, and re-evaluation of (i) hand placement on the patient, (ii) depth of compression, (iii) rate of compression, or (iv) recoil.

16. The method of claim 1, wherein receiving the physiologic monitoring data comprises:
receiving, from a metabolic sensor, an indication of a metabolic rate of the patient;
receiving, from a blood pressure sensor, an indication of a blood pressure of the patient;
receiving, from a depth sensor, an indication of a depth of compression applied during cardiopulmonary resuscitation (CPR); and
receiving, from an ultrasound sensor, an indication of vessel area and flow profile over time;
the method further comprising:
based on a combination of the physiologic monitoring data from the plurality of sensors and the respective quality indicator for the physiologic monitoring data, outputting the caregiver feedback by the computing device indicative of one or more of: whether CPR appears to be moving a sufficient amount of oxygenated blood, and re-evaluation of (i) hand placement on the patient, (ii) depth of compression, (iii) rate of compression, or (iv) recoil.

17. The method of claim 1, wherein receiving the physiologic monitoring data comprises:
receiving, from external pressure sensors, tactile pressure applied to a chest of a patient during cardiopulmonary resuscitation (CPR); and
receiving, from external ultrasound sensors, an indication of a location of a heart of the patient;
the method further comprising:
based on a combination of the physiologic monitoring data from the plurality of sensors and the respective quality indicator for the physiologic monitoring data, outputting the caregiver feedback by the computing device indicative of whether hand placement for CPR needs to be adjusted.

18. The method of claim 1, wherein receiving the physiologic monitoring data comprises:
receiving, from a blood pressure sensor, an indication of a blood pressure of the patient;
receiving, from an electrocardiogram (ECG) sensor, one or more cardiac electrical signals;
receiving, from an oxygen sensor, an indication of oxygen inhaled by the patient;
receiving, from a carbon dioxide sensor, an indication of carbon dioxide expelled by the patient; and
receiving, from external ultrasound sensors, an indication of a location of a heart of the patient;
the method further comprising:
based on a combination of the physiologic monitoring data from the plurality of sensors and the respective quality indicator for the physiologic monitoring data, outputting the caregiver feedback by the computing device indicative of one of return of spontaneous circulation (ROSC) or pulseless electrical activity (PEA).

19. The method of claim 1, wherein receiving the physiologic monitoring data comprises:
receiving, from an electrocardiogram (ECG) sensor, one or more cardiac electrical signals;
receiving, from a lactate sensor, an indication of an analysis of blood of the patient; and
receiving, from a temperature sensor, an indication of patient temperature;
the method further comprising:
based on a combination of the physiologic monitoring data from the plurality of sensors and the respective quality indicator for the physiologic monitoring data, outputting the caregiver feedback by the computing device indicative of a reminder to check for sepsis in the patient.

20. A non-transitory computer-readable medium having stored therein a plurality of executable instructions, which when executed by a computing device having a processor causes the computing device to perform functions comprising:
receiving physiologic monitoring data from a plurality of sensors coupled to a patient during a patient care event, wherein each of the plurality of sensors has an associated motion, position, and/or orientation (MPO) sensor external from the plurality of sensors and configured to output information indicating a measurement of patient motion during the patient care event;
based on the physiologic monitoring data indicating a substantive change, interrogating the MPO sensor associated with a particular one of the plurality of sensors outputting the physiologic monitoring data indicating the substantive change;
receiving the information indicating the measurement of patient motion during the patient care event from the interrogated MPO sensor;
determining whether the measurement of patient motion is above a threshold for the particular one of the plurality of sensors during the patient care event;
based on determining whether the measurement of patient motion is above the threshold for the particular one of the plurality of sensors, generating, for the physiologic monitoring data received from each sensor of the plurality of sensors, a respective quality indicator;
analyzing, by the computing device, (i) a combination of the physiologic monitoring data from the plurality of sensors and (ii) the respective quality indicator for the physiologic monitoring data to generate a response dependent upon the combination of the physiologic monitoring data as weighted by the respective quality indicator; and
based on analyzing (i) the combination of the physiologic monitoring data from the plurality of sensors and (ii) the respective quality indicator for the physiologic monitoring data, outputting caregiver feedback by the computing device according to the response.

21. A system comprising:
a non-transitory computer-readable medium having stored therein a plurality of executable instructions; and
a processor adapted to execute the plurality of executable instructions to:
receiving physiologic monitoring data from a plurality of sensors coupled to a patient during a patient care event, wherein each of the plurality of sensors has an associated motion, position, and/or orientation (MPO) sensor external from the plurality of sensors and configured to output information indicating a measurement of patient motion during the patient care event;
based on the physiologic monitoring data indicating a substantive change, interrogating the MPO sensor associated with a particular one of the plurality of sensors outputting the physiologic monitoring data indicating the substantive change;

receiving the information indicating the measurement of patient motion during the patient care event from the interrogated MPO sensor;

determining whether the measurement of patient motion is above a threshold for the particular one of the plurality of sensors during the patient care event;

based on determining whether the measurement of patient motion is above the threshold for the particular one of the plurality of sensors, generating, for the physiologic monitoring data received from each sensor of the plurality of sensors, a respective quality indicator;

analyze (i) a combination of the physiologic monitoring data from the plurality of sensors and (ii) the respective quality indicator for the physiologic monitoring data to generate a response dependent upon the combination of the physiological monitoring data as weighted by the respective quality indicator; and based on analyzing (i) the combination of the physiologic monitoring data from the plurality of sensors and (ii) the respective quality indicator for the physiologic monitoring data, output caregiver feedback by the computing device according to the response.

22. A method performed by a computing device executing instructions stored in data storage, the method comprising:

receiving physiologic monitoring data from a plurality of sensors coupled to a patient during a patient care event, wherein each of the plurality of sensors has an associated motion, position, and/or orientation (MPO) sensor external from the plurality of sensors and configured to output information indicating a measurement of patient motion during the patient care event;

determining an expected correlation between multiple of the physiologic monitoring data;

based on determining a lack of the expected correlation between multiple of the physiologic monitoring data, interrogating the MPO sensors to receive the information indicating the measurement of patient motion during the patient care event;

determining whether the measurement of patient motion is above a threshold for the plurality of sensors during the patient care event;

based on determining whether the measurement of patient motion is above the threshold for the plurality of sensors, generating, for the physiologic monitoring data received from each sensor of the plurality of sensors, a respective quality indicator;

analyzing, by the computing device, (i) a combination of the physiologic monitoring data from the plurality of sensors and (ii) the respective quality indicator for the physiologic monitoring data to generate a response dependent upon the combination of the physiologic monitoring data as weighted by the respective quality indicator; and based on analyzing (i) the combination of the physiologic monitoring data from the plurality of sensors and (ii) the respective quality indicator for the physiologic monitoring data, outputting caregiver feedback by the computing device according to the response.

23. A method performed by a computing device executing instructions stored in data storage, the method comprising:

receiving physiologic monitoring data from a plurality of sensors coupled to a patient during a patient care event, wherein each of the plurality of sensors has an associated motion, position, and/or orientation (MPO) sensor external from the plurality of sensors and configured to output information indicating a measurement of patient motion during the patient care event;

based on the physiologic monitoring data indicating a substantive change, interrogating the MPO sensor associated with a particular one of the plurality of sensors outputting the physiologic monitoring data indicating the substantive change;

receiving the information indicating the measurement of motion, orientation, or position of a part or a whole of a body of the patient during the patient care event from the interrogated MPO sensor; and generating one or more context indicators displayed in conjunction with a display of the physiologic monitoring data, wherein the context indicators graphically convey an amount of motion exhibited by the part or the whole of the body of the patient.

24. The method of claim 23, wherein generating the one or more context indicators comprises generating the context indicators to graphically convey the orientation of the position of the part or the whole of the body of the patient.

25. The method of claim 23, wherein generating the one or more context indicators comprises generating the context indicators to provide one or more snapshot indications of patient motion or position.

26. The method of claim 23, wherein generating the one or more context indicators comprises generating the context indicators to provide a continuous indication of patient motion or position.

* * * * *